(12) United States Patent
Wilson et al.

(10) Patent No.: US 8,935,001 B2
(45) Date of Patent: Jan. 13, 2015

(54) SYSTEM AND METHOD FOR ESTABLISHING AND/OR MAINTAINING PROPER ALIGNMENT OF A ROBOTIC TRANSFER MECHANISM

(71) Applicant: bioMeriéux, Inc., Durham, NC (US)

(72) Inventors: Mark S. Wilson, Hillsborough, NC (US); Richard Trigg, St. Charles, MO (US); Walter Clynes, O'Fallon, MO (US)

(73) Assignee: bioMeriéux, Inc., Durham, NC (US)

( * ) Notice: Subject to any disclaimer, the term of this patent is extended or adjusted under 35 U.S.C. 154(b) by 11 days.

(21) Appl. No.: 13/827,974

(22) Filed: Mar. 14, 2013

(65) Prior Publication Data

US 2013/0274913 A1    Oct. 17, 2013

Related U.S. Application Data

(60) Provisional application No. 61/617,440, filed on Mar. 29, 2012.

(51) Int. Cl.
| | | |
|---|---|---|
| *G06F 7/00* | (2006.01) | |
| *B65G 1/04* | (2006.01) | |
| *F16H 7/12* | (2006.01) | |
| *G01N 35/00* | (2006.01) | |
| *B25J 9/02* | (2006.01) | |
| *B25J 9/10* | (2006.01) | |
| *B25J 15/00* | (2006.01) | |
| *B25J 15/02* | (2006.01) | |

(52) U.S. Cl.
CPC ............... *B65G 1/0478* (2013.01); *F16H 7/12* (2013.01); *G01N 35/0099* (2013.01); *B25J 9/023* (2013.01); *B25J 9/1045* (2013.01); *B25J 15/0038* (2013.01); *B25J 15/0213* (2013.01); *B25J 15/0226* (2013.01)
USPC ........... 700/213; 700/214; 700/222; 700/229; 700/245; 700/258

(58) Field of Classification Search
None
See application file for complete search history.

(56) References Cited

U.S. PATENT DOCUMENTS

| | | |
|---|---|---|
| 2005/0045815 A1 | 3/2005 | Buy |
| 2005/0283274 A1 | 12/2005 | Kleinschmitt |
| 2010/0129789 A1* | 5/2010 | Self et al. ........................... 435/5 |
| 2011/0124028 A1 | 5/2011 | Robinson et al. |

* cited by examiner

*Primary Examiner* — Yolanda Cumbess

(57) ABSTRACT

The present invention is directed to a system and method for establishing and/or maintaining proper alignment of a transfer mechanism. More specifically, the present invention is directed to an alignment system and method having one or more of: (a) a laser alignment device operable to providing precise locational coordinates for alignment of a robotic transfer mechanism relative to a holding structure; (b) an alignment tool for aligning a laser alignment device relative to robotic transfer mechanism; (c) lead in ramps to properly guide an individual specimen container into a holding well; and/or (d) a belt tensioning device for maintaining proper tension on one or more timing belts.

25 Claims, 20 Drawing Sheets

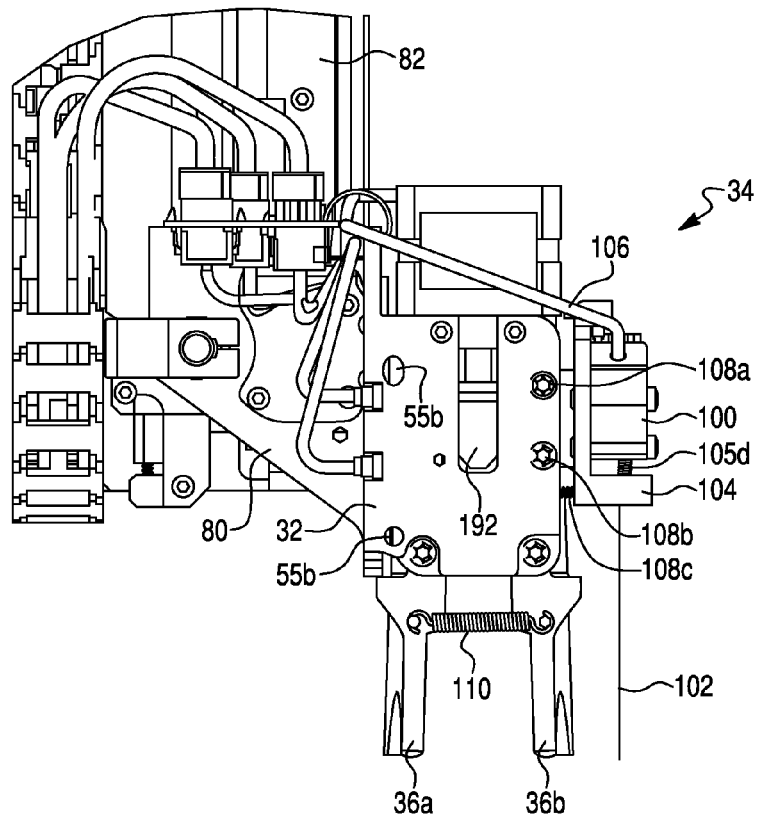
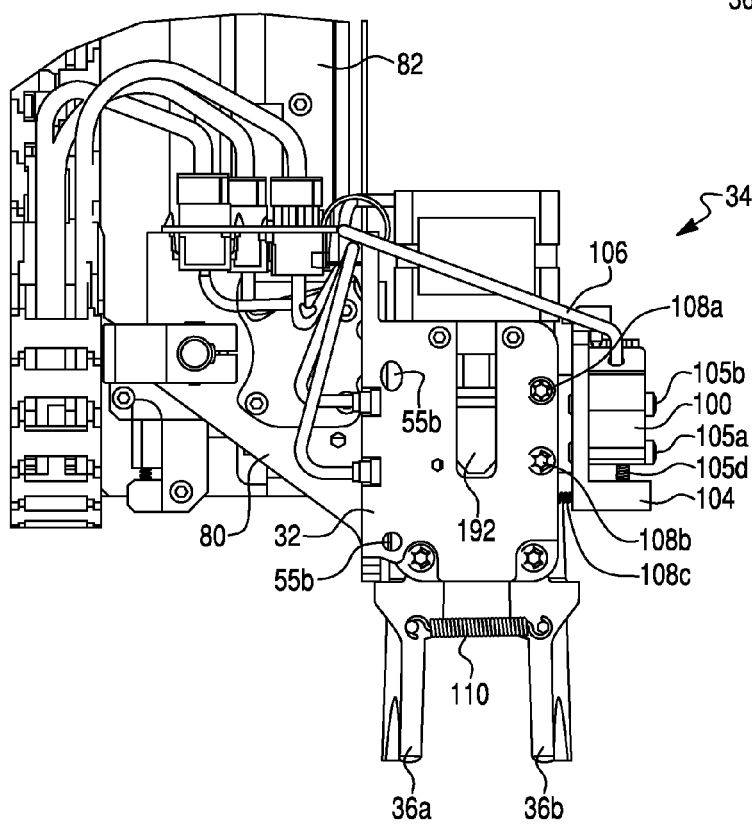

Fig. 9A
Fig. 9B
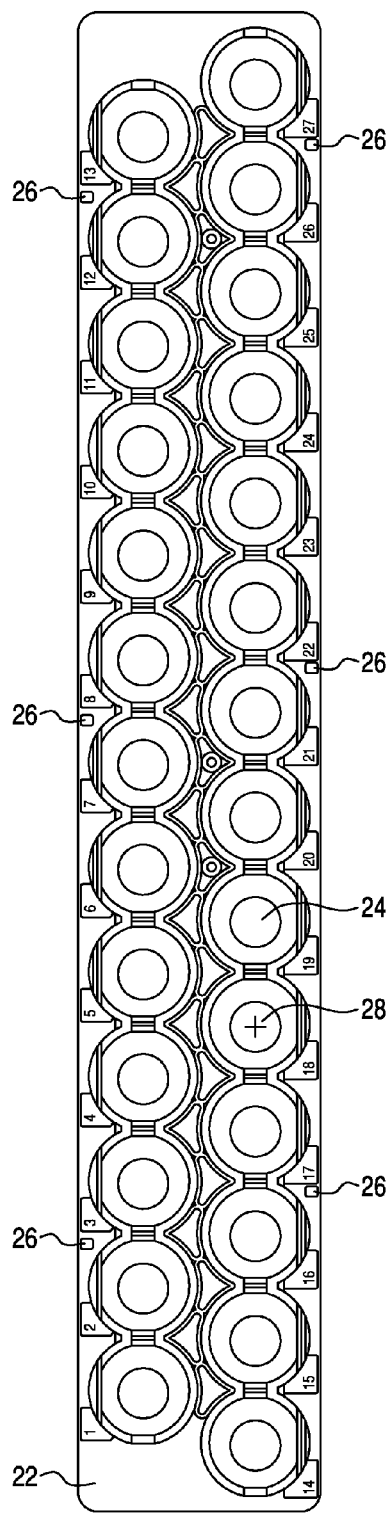
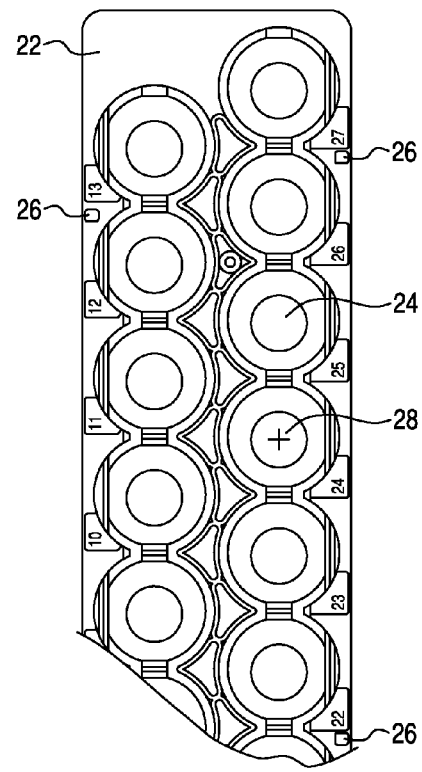

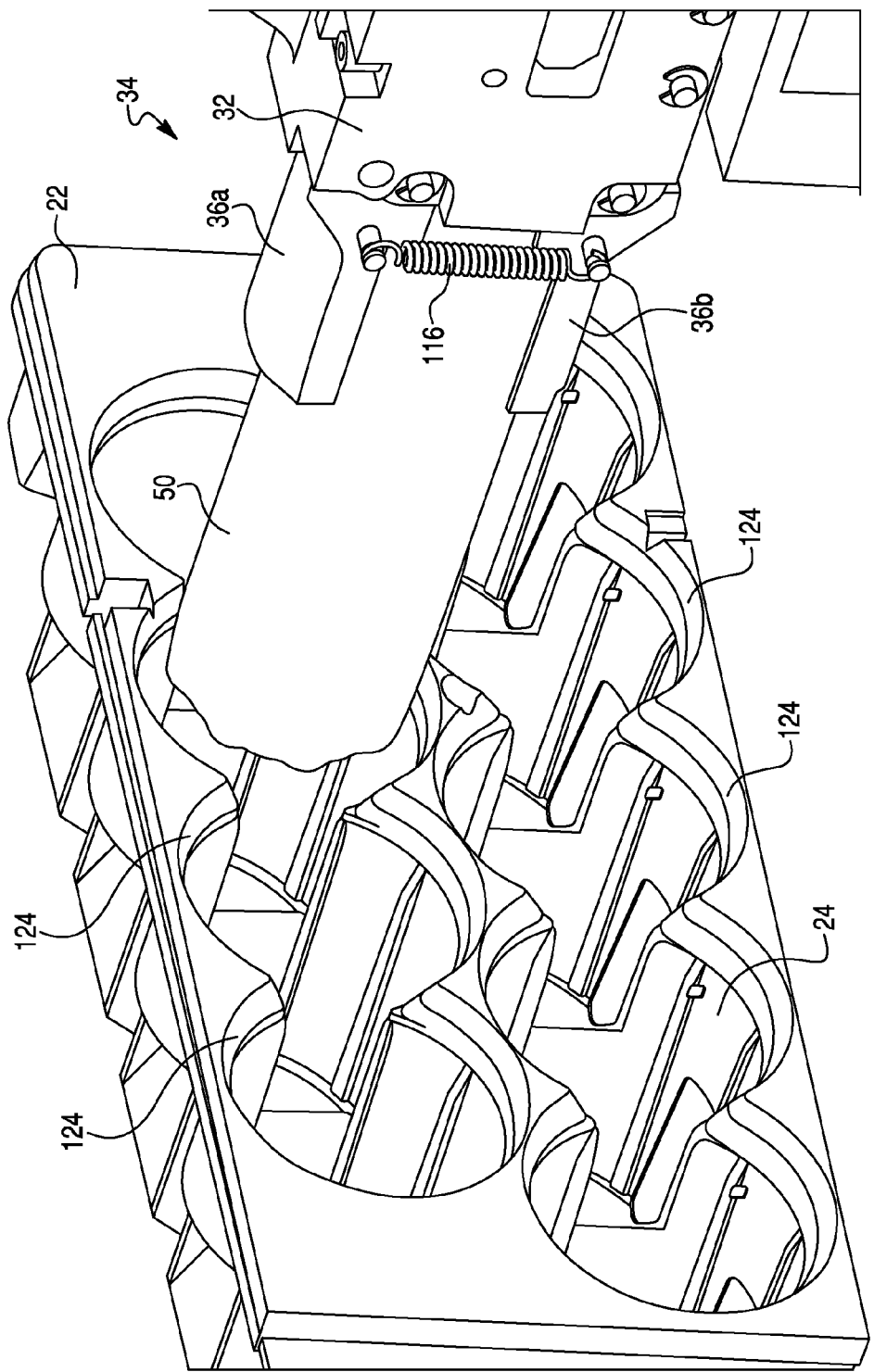

Fig. 21

| Laser Position In Gage | Description | LED Return Signal |
|---|---|---|
| 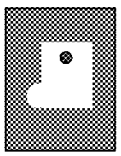 | Position laser beam relative to a fiducial of the alignment tool. | Low |
|  | Move laser beam to left in x-axis until laser just triggers on edge of target. The laser sensor return LED will go "high". Lock down x-axis alignment screws. Now laser is constrained to move vertically. | High |
|  | Move laser beam down in y-axis. When beam leaves the vertical edge, the sensor return LED indicator will go "low". | Low |
|  | Continue to move laser beam down in y-axis until the sensor return LED indicator goes "high". Now the laser sensor is aimed properly. Lock down y-axis alignment screw. Now laser is constrained to move vertically. | High |

SYSTEM AND METHOD FOR ESTABLISHING AND/OR MAINTAINING PROPER ALIGNMENT OF A ROBOTIC TRANSFER MECHANISM

CROSS REFERENCE TO RELATED APPLICATION

This application claims the benefit of U.S. Provisional Patent Application No. 61/617,440, entitled, "System and Method for Establishing and/or Maintaining Proper Alignment of a Robotic Transfer Mechanism", filed Mar. 29, 2012, which is incorporated herein.

FIELD OF THE INVENTION

The present invention is directed to a system and method for establishing and/or maintaining proper alignment of a robotic transfer mechanism. More specifically, the present system is directed to an alignment system or means for proper alignment of a robotic transfer mechanism for precise loading, transfer and/or unloading of specimen containers (e.g., culture bottles) within an automated microbial detection systems.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles. A small quantity of blood is injected through an enclosing rubber septum into a sterile bottle containing a culture medium, and the bottle is then incubated at 37° C. and monitored for microorganism growth.

Instruments currently exist on the market that detect the growth of a microorganism in a biological sample. One such instrument is the BacT/ALERT® 3D instrument of the present assignee bioMérieux, Inc. The instrument receives a blood culture bottle containing a blood sample, e.g., from a human patient. The instrument incubates the bottle and periodically during incubation an optical detection unit in the incubator analyzes a colorimetric sensor incorporated into the bottle to detect whether microbial growth has occurred within the bottle. The optical detection unit, bottles and sensors are described in the patent literature, see U.S. Pat. Nos. 4,945,060; 5,094,955; 5,162,229; 5,164,796; 5,217,876; 5,795,773; and 5,856,175, the entire content of each of which is incorporated by reference herein. Other prior art of interest relating generally to the detection of microorganisms in a biological sample includes the following U.S. Pat. No. 5,770,394, U.S. Pat. No. 5,518,923; U.S. Pat. No. 5,498,543, U.S. Pat. No. 5,432,061, U.S. Pat. No. 5,371,016, U.S. Pat. No. 5,397,709, U.S. Pat. No. 5,344,417 and its continuation U.S. Pat. No. 5,374,264, U.S. Pat. No. 6,709,857; and U.S. Pat. No. 7,211,430, the entire content of each of which is incorporated by reference herein.

Fully automated microbial detection systems are also known in the art, see, for example, U.S. 2011/0124028, the content of which is hereby incorporated by reference. The fully automated microbial detection system disclosed therein can include one or more of the following features: (1) a housing, enclosing an interior chamber (e.g., an incubation chamber); (2) an automated loading mechanism for loading one or more containers into the interior chamber of the system; (3) an automated container management mechanism or locator device for moving or locating a container among various work-flow stations within the system; (4) an automated transfer mechanism, for transfer of a container within the system; (5) one or more container holding structures for holding a plurality of specimen containers, optionally provided with an agitation assembly; (6) a detection unit for detection of microbial growth; and/or (7) a mechanism for automated unloading of a specimen container from the system. However, as one of skill may appreciate, a need remains for developing systems, devices and methods for establishing and/or maintaining proper alignment of one or more of these automated mechanisms, such as the automated transfer mechanism for precise loading, transfer and/or unloading of specimen containers (e.g., culture bottles) within the automated microbial detection systems.

The disclosed automated detection system and alignment system comprises a fully automated microbial detection system operative to detect growth within a specimen container containing a test sample (e.g., a biological sample) as being positive for microbial agent presence. The systems and methods of this disclosure have the potential to: (a) reduce laboratory labor and user errors; (b) improve sample tracking, traceability and information management; (c) interface to laboratory automation systems; (d) improve work-flow and ergonomics; (e) deliver clinically relevant information; (f) faster results. The alignment systems and methods disclosed herein improve system reliability by improving robotic alignment and allow for accuracy or precise loading, transfer and/or unloading of specimen containers (e.g., culture bottles) within the automated microbial detection systems.

Many further advantages and benefits over the prior art will be explained below in the following detailed description.

SUMMARY OF THE INVENTION

In one aspect, the present invention is directed to an alignment system for establishing and/or maintaining alignment of an automated robotic transfer mechanism in an automated detection system relative to a holding structure for holding one or more specimen containers, comprising: (a) an automated detection system for processing specimen containers, said detection system having a housing enclosing an interior chamber; (b) a holding structure within said interior chamber said holding structure having one or more holding wells for holding individual specimen containers, wherein said holding structure further comprises one or more fiducials; (c) an automated robotic transfer mechanism for the automated transfer of said specimen container within said interior chamber, said automated robotic transfer mechanism further comprising a gripping mechanism and a laser alignment device, said laser alignment device operable to detect said one or more fiducials and thereby determine the home position of said automated transfer mechanism relative to said holding structure; and (d) a controller for determining the x and y positions of said one or more holding wells relative to the home position of said automated transfer mechanism relative to said holding structure. In other embodiments, the laser alignment device can be used to locate and align the robotic transfer mechanism to other mechanisms or devices that interface with the robotic transfer mechanism, such as, an indexer, container pick-up station, waste chute, container return port or chute.

In one embodiment, the laser alignment device is adjustable, and can be adjusted to align the laser alignment device relative to the gripping mechanism of the robotic transfer mechanism. The laser alignment device can be attached to an adjustable block, said adjustable block having a pivot screw and a locking screw operable for adjusting, and then locking, the laser alignment device to establish proper alignment of the laser alignment device with respect to the robotic transfer mechanism, and thereby with the gripping mechanism. As described elsewhere herein, an alignment tool having a fiducial can be used to align the laser alignment device with respect to the robotic transfer mechanism. In other embodiments, the alignment system may further comprises a first and/or second adjustment mechanism for adjustment of said laser beam, relative to said one or more fiducials, in an x-axis and/or y-axis, respectively.

In another embodiment, the laser alignment device of the alignment system identifies one or more fiducials located on said holding structure, wherein by locating said one or more fiducials said laser alignment device provides precise x-, and y-position, or coordinates, of the individual wells relative to the robotic transfer mechanism can be determined, or calculated, e.g., by a controller.

In another embodiment, an alignment tool, or more specifically, a removable positioning piece thereof can be used to establishing and/or maintaining proper alignment of a robotic transfer mechanism with a pick-up station, which may be part of an indexer or loading station, as described herein below. In accordance with this embodiment, the removable positioning piece is operable to set, or ensure, proper co-axial alignment of the gripping mechanism with respect to the pick-up station.

In yet another embodiment, the individual holding wells of the alignment system may further comprise lead in ramps to guide an individual specimen container into said holding well, and thereby correct for any small misalignment of said specimen container as said container is loaded into an individual holding well. The lead in ramps may comprise a plurality of angled lead in nodes or a continuous tapered lead in ramp.

In still other embodiments, the alignment system may further comprising one or more belt tensioning devices for maintaining proper tension on one or more belts, such as drive belts, timing belts, or chain drives. In accordance with this embodiment, the belt tensioning device will include a mechanism or device for providing a force operable for maintaining proper tension on a belt. The mechanism or device can be a compression spring, one or more disk washer, such as a Belleville washer, a plurality of disk washers arranged in series, or a plurality of disk washers arranged in parallel, or a combination of series and parallel orientation.

In still another embodiment, the alignment system further comprising a robotic head and gripping mechanism, the gripping mechanism having at least 2 gripping fingers (e.g., from 2 to 6 gripping fingers). In one embodiment, the gripping fingers may comprise 2 opposable semi-circular shaped gripping fingers, wherein said semi-circular shaped gripping fingers define a gripping cavity operable to securely grip and/or hold a specimen container (e.g., a circular or semi-circular specimen container). The semi-circular shaped gripping fingers may further comprise an opposable pair of angled alignment nodes operable to align and center said container within said gripping cavity, for example, such that the centerline of said specimen container is aligned with the centerline of said gripping mechanism or gripping cavity, i.e., co-axial. The gripping fingers may also comprises a soft or elastomeric gripping pad operable to securely hold said container and/or limit movement of said container relative to said gripping fingers, while the angled alignment nodes ensure proper co-axial alignment of said container within said gripping mechanism.

In another aspect, the present invention is directed to a belt tensioning device for maintaining proper tension on a transfer mechanism timing belt, comprising: (a) a robotic transfer mechanism having at least one axis, a robotic head movable along said at least one axis, and a timing belt; and (b) a tensioning device operable to provide tension to said timing belt, said tensioning device comprising: (i) a slide plate coupled to a tensioner housing and to an idler pulley; (ii) a fixed block and threaded shaft, wherein said threaded shaft is movable relative to said fixed block; (iii) a tensioner housing having a counter bore, a plunger and a compression mechanism operable to provide a force, wherein said plunger is movable relative to said counter bore and said compression mechanism; and wherein said threaded shaft is operable to drive said plunger into said counter bore, thereby compressing said compression mechanism and provide tension to said timing belt.

In yet another embodiment, the present invention is also directed to a belt tensioning device for maintaining proper tension on a transfer mechanism timing belt, comprising: (a) a robotic transfer mechanism having at least one axis, a robotic head movable along said at least one axis, and a timing belt; and (b) a tensioning device operable to provide tension to said timing belt, said tensioning device comprising: (i) a stationary block having a threaded plunger, a compression mechanism and a plurality of teeth operable to engage a first end of said timing belt, wherein said stationary block is coupled to a carriage supporting the robotic transfer mechanism; and (ii) a slidable block having a counter bore, a threaded plunger and a plurality of teeth for engaging a second end of said timing belt, wherein said plunger is movable relative to said counter bore and said compression mechanism; and wherein said threaded plunger is operable to drive said plunger into said counter bore, thereby compressing said compression mechanism and provide tension to said timing belt.

In still another aspect, the present invention is directed to a method for establishing and/or maintaining alignment of an automated transfer mechanism relative to a holding structure, the method comprising: (a) providing an automated robotic transfer mechanism having a robotic head, a gripping mechanism for gripping a specimen container around a centerline of said gripping mechanism, and a laser alignment device attached to the robotic head, said laser alignment device; (b) providing a holding structure comprising a plurality of holding wells and one or more fiducials; (c) detecting said one or more fiducials with said laser alignment device, thereby setting a home position for said automated robotic transfer mechanism relative to said holding structure; and (d) determining the x- and y-positions of said one or more holding wells using a controller. In one embodiment, the laser alignment device is operable for establishing and/or maintaining proper alignment of the robotic transfer mechanism with respect to one or more mechanisms or devices that interface with the robotic transfer mechanism, selected from the group comprising of an indexer, a container pick-up station, a holding structure, a waste chute, and a container return port or chute.

BRIEF DESCRIPTION OF THE FIGURES

The various inventive aspects will become more apparent upon reading the following detailed description of the various embodiments along with the appended drawings, in which:

As shown in FIG. 3A, the robotic head is located at a first end of the pivot plated and in a horizontal orientation, such that the specimen container is also orientated in a horizontal orientation. In FIG. 3B, the robotic head is shown located at a second end of the pivot plate and in a vertical orientation, such that the specimen container is also orientated in a vertical orientation.

FIG. 5A-5B are perspective close-up views of the robotic head, gripping mechanism and laser of the automated transfer mechanism shown in FIGS. 1-3B.

FIG. 8A shows a perspective view of the detachable positioning piece of a 2-part alignment tool, relative to the container pick-up station. FIG. 8B shows a perspective view of a 2-part alignment tool and use thereof for proper co-axial alignment of the robotic head and gripping mechanism with the container pick-up station. FIG. 8C shows a perspective view of the robotic head and gripping mechanism "picking up" a specimen container from the container pick-up station.

FIGS. 9A-9B are front elevation views of a holding structure as shown in FIGS. 1-2.

FIG. 14 is a perspective view of a robotic head and gripping mechanism shown loading a specimen container into a well of a holding structure having a lead in ramp in accordance with one embodiment of the invention.

FIG. 21 shows a table illustrating a method for proper alignment of adjustable laser device using an alignment tool.

DETAILED DESCRIPTION OF THE INVENTION

Figure 1:
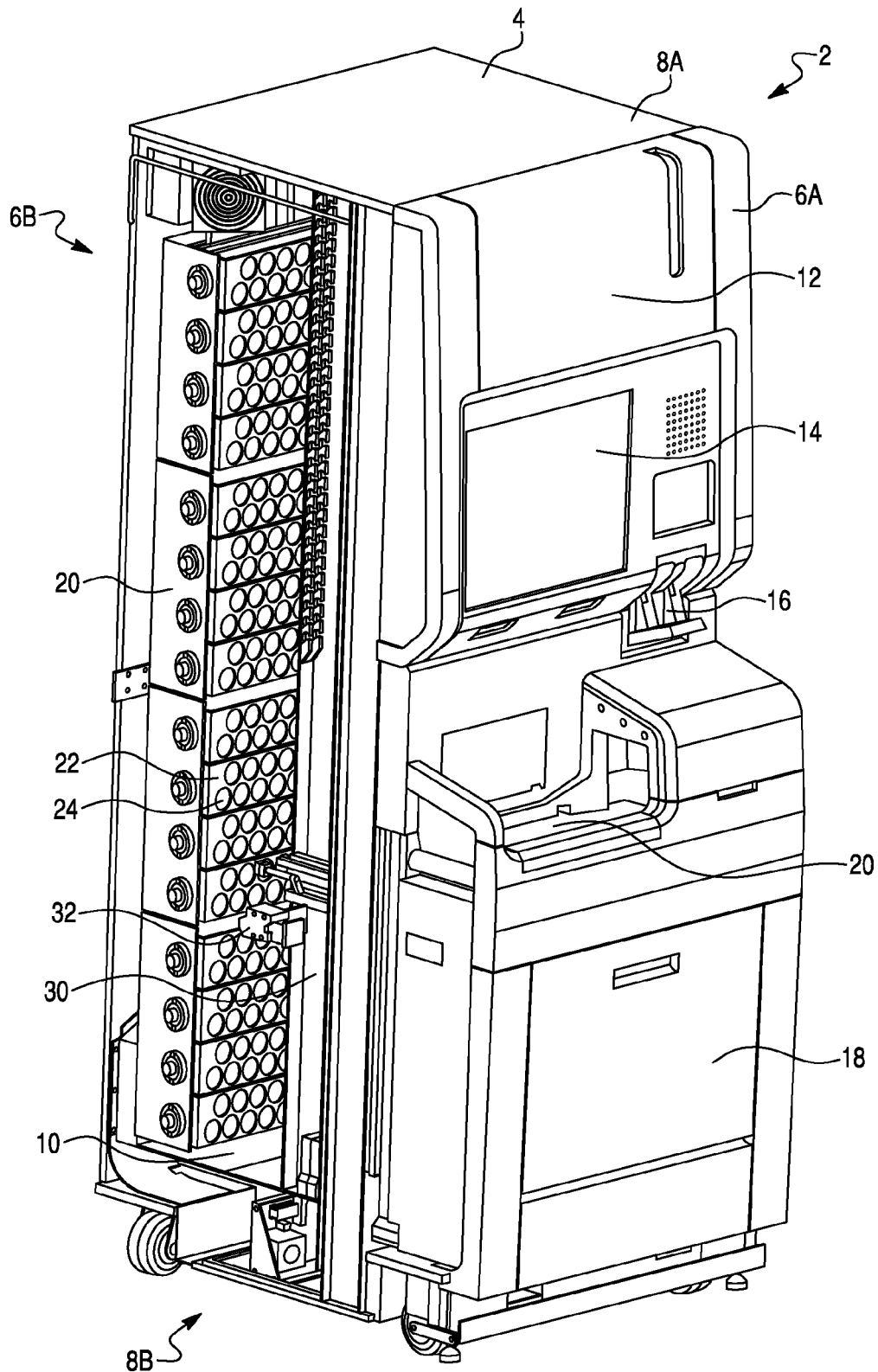
FIG. 1 shows a side perspective view of a detection system with the left side panel removed to show internal components of the system. As shown, the detection system includes a plurality of vertically stacked holding structures and as automated transfer mechanism.

The present disclosure is directed to an alignment system and method for establishing and/or maintaining proper alignment of an automated transfer mechanism. In order to better appreciate how the illustrated embodiment of the alignment system and method operate, this specification describes the alignment system and method in the context of a particular automated detection system and a particular automated transfer mechanism for the transfer of specimen container within the detection system. However, as one of skill in the art will appreciate the alignment system and method can be practiced in other embodiments, that variations from the specific embodiments disclosed herein can be arrived at to suit particular implementations, and that therefore the present description of a preferred embodiment and best mode for practicing the invention is provided by way of illustration and not limitation.

System Overview

An alignment system and method for establishing and/or maintaining proper alignment of an automated transfer mechanism operable to pick-up a specimen container from a pick-up station, transfer and loading and/or unloading the specimen container, into or from, a plurality of holding wells is described herein. In one aspect, the alignment system and method operate to establish and/or maintain proper alignment of an automated transfer mechanism within an automated detection system or instrument for non-invasive detection of the presence of a microbial agent (e.g., a microorganism) in a test sample contained within a sample container. In another aspect, the alignment system and method operate to establish and/or maintain proper alignment of an automated transfer mechanism relative to other mechanisms or devices within an automated detection system or instrument that interface with the robotic transfer mechanism, such as, for example, an indexer, a container pick-up station, a holding structure and one or more holding wells contained therein, a waste chute, and a container return port or chute. In general, any known test sample (e.g., a biological sample) can be used. For example, the test sample can be a clinical or non-clinical sample suspected of containing one or more microbial agents. Clinical samples, such as a bodily fluid, include, but are not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Non-clinical samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. In one embodiment, the biological sample tested is a blood sample.

In accordance with this aspect of the present invention, the alignment system and method described herein may be practiced in conjunction with the automated detection apparatus described in further detail in U.S. 2011/0124028, which is incorporated herein by reference. Briefly, the automated detection apparatus for rapid non-invasive detection of microorganism growth in a test sample may comprise one or more of the following features: (a) a sealable specimen container having an internal chamber with a culture medium disposed therein for culturing any microorganisms that may be present in the test sample; (b) a housing enclosing an interior chamber (e.g., a climate controlled chamber or incubation chamber); (c) a holding structure contained within the interior chamber and having a plurality of wells for holding individual specimen containers; (d) an automated loading mechanism for automated loading of a specimen container into the interior chamber; (e) a container locator device operable to move the specimen container to one or more container work-flow stations for processing, including, for example, a container pick-up station or location; (f) an automated transfer mechanism located within the interior chamber for the automated transfer of the specimen container within the interior chamber; (g) a detection unit located within the interior chamber for the detection of microorganism growth in a specimen container and/or (h) an automated unloading mechanism for the unloading of "positive" and/or "negative" specimen containers.

In another aspect of the present invention, the alignment system disclosed herein may comprise one or more of the following features: (1) a laser alignment device operable to provide precise locational coordinates (or x-, and y-positions), and/or alignment of, a robotic transfer mechanism relative to one or more mechanisms or devices that interface with the robotic transfer mechanism, such as, a holding structure comprising a plurality of wells, and/or a container pick-up station or location, thereby allowing for proper pick-up, transfer and loading and/or unloading of specimen containers; (2) an alignment tool for establishing and/or maintaining proper alignment of the laser alignment device relative to the robotic transfer mechanism, to establish or ensure proper alignment of the robotic transfer mechanism relative to one or more other mechanisms or devices that interface with the robotic transfer mechanism; (3) lead in ramps in conjunction with individual holding wells to guide an individual specimen container into the holding well, thereby correcting for, or accommodating any misalignment of a specimen container as the container is loaded into an individual holding well; (4) a gripping mechanism having at least 2 gripping fingers, wherein the gripping fingers define a gripping cavity, and a centerline, the gripping mechanism operable to securely grip and/or hold a specimen container about the centerline of the gripping mechanism; and/or (5) one or more belt tensioning devices for providing and/or maintaining proper tension on one or more timing belts of the automated transfer mechanism.

Detection System

Referring now to the Figures, FIG. 1 illustrates an automated detection system in which the alignment system and/or method described herein may be used. As shown in FIG. 1, an automated detection system 2 may comprise a housing 4 having front and back panels 6A, 6B, side panels (not shown) and top and bottom panels 8A, 8B, which enclose an interior chamber 10 (e.g., a climate controlled chamber or incubation chamber) for promoting and/or enhancing microbial growth within the system. The housing may also include an operable access door 12 for providing a user or technician access to the enclosed interior chamber 10 (e.g., a climate controlled or incubation chamber). The door 12 may also have one or more user interface displays 14, one or more container ports 16, for retrieval of "positive" containers, and a lower access panel 18, typically for housing a waste container for "negative" containers. As shown in FIG. 1, the automated detection system 2 may also include an automated loading mechanism 20 for loading specimen containers into the system. The use of an automated loading mechanism 20 allows for specimen containers to be loaded into the interior chamber 10 without opening the access door 12, which would disrupt the enclosed interior chamber 10.

The automated detection system will also typically include a holding means or structure 20 for holding one or more individual specimen containers, for example, a plurality of individual specimen containers. The holding means or structure 20 of the detection system 2 can take a variety of physical configurations for handling a plurality of individual specimen containers so that a large number of containers (e.g., 200 or 400 containers, depending on the specific holding structures used) can be processed simultaneously. The holding means or structure can be used for storage, agitation and/or incubation of the specimen containers. One possible configuration is shown in FIG. 1. However, as one of skill in the art will appreciate, other designs for the holding means or structure are possible and contemplated in the practice of the present invention.

Figure 2:
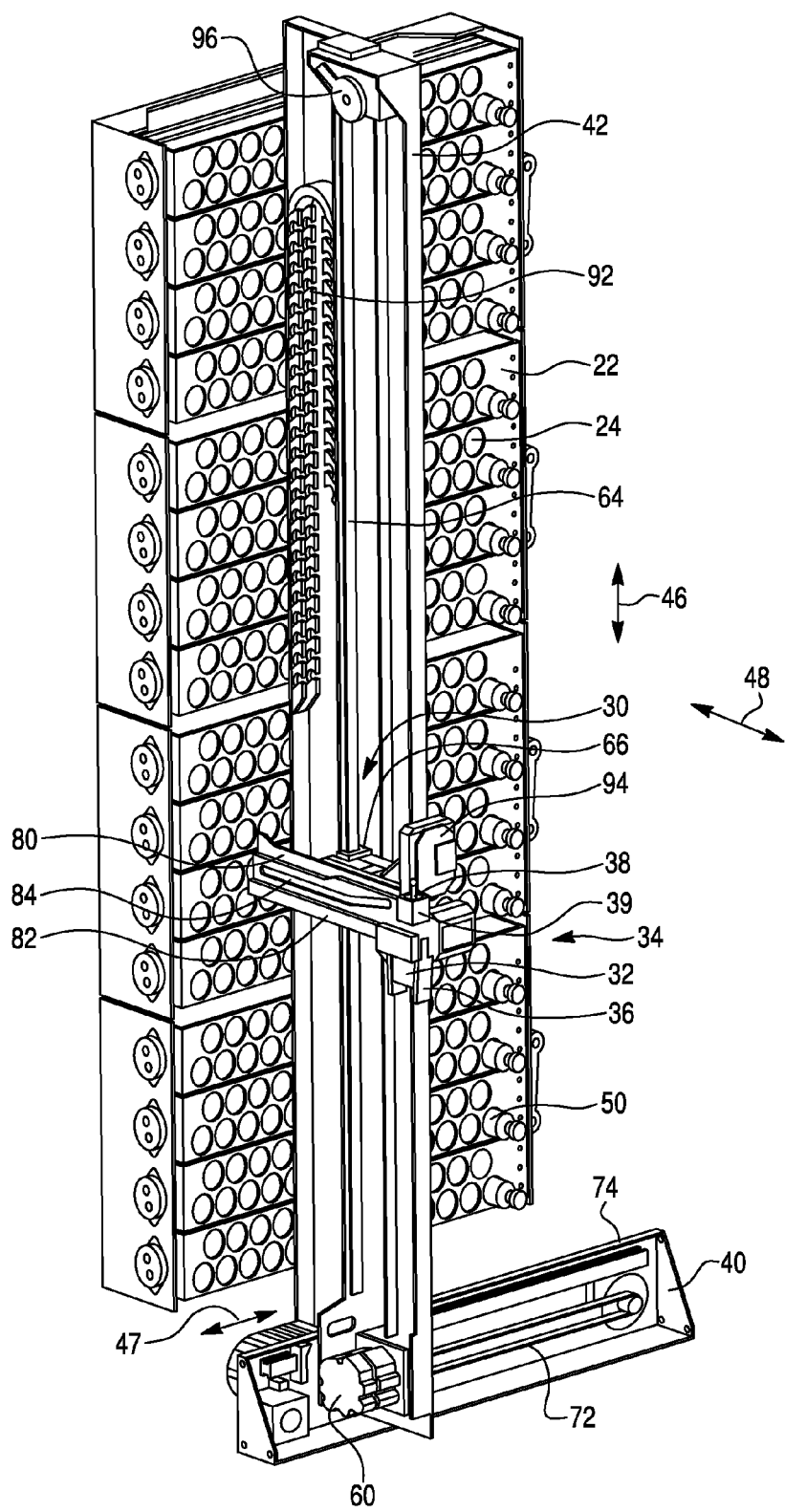
FIG. 2 is a perspective view of the holding structure and automated transfer mechanism shown in FIG. 1. As shown, in this embodiment, the automated transfer mechanism comprises a lower horizontal support, a vertical support, a pivot plate and a robotic head for transferring a specimen container within a detection apparatus. For clarity, the holding structure and automated transfer mechanism are shown isolated from the detection apparatus.

As shown in FIG. 1-2, the illustrated system includes a plurality of vertically stacked holding structures 20. One possible configuration uses a plurality of vertically stacked container holding structures or racks 22 each having one or more individual specimen container receiving structures or wells 24 each for holding individual specimen containers. In one embodiment, the holding structures or racks 22 may include a plurality of receiving structures or wells 24 each for holding individual specimen containers. In accordance with this embodiment, two or more vertically stacked holding structures or racks 22 can be used. For example, from about 2 to about 40, from about 2 to about 20, or about 16 vertically stacked holding structures or racks can be used. Referring again to FIGS. 1-2, the detection system 2 includes a climate controlled interior chamber (or incubation chamber) 10, having sixteen (16) vertically disposed holding structures or racks 22 each having one or more individual container receiving structures or wells 24 therein. In one embodiment, each holding structure or rack 22 may comprise one or more receiving structures of wells 24 therein. In another embodiment, each holding structure or rack 22 may comprise from about 2 to about 40, from about 2 to about 30, or from about 2 to about 20 receiving structures of wells 24 therein. In yet another embodiment, as shown in FIGS. 1-2, the holding structures or racks 24 may comprise two (2) staggered rows of receiving structures or wells 24.

As one of skill in the art would appreciate, each of the individual container receiving structures or wells 24 has a specific X and Y coordinate position or address, where X is the horizontal location and Y is the vertical location of each container receiving structure or well 24. In accordance with the present invention, the individual wells 24 can be accessed by an automated transfer mechanism or robotic transfer mechanism or arm. For example, as shown in FIGS. 1-3B, and described in greater detail hereinbelow, the automated transfer mechanism 30, for example, a robotic transfer mechanism can operate to move a robotic head 32, and thus, a specimen container, to a specific well 24 (i.e., a specific X, Y position) in the rack 22 and deposit the container therein. In another embodiment, the X and Y position for the centerline 28 (see, e.g., FIGS. 9A-9B) of an individual well can be determined, using a controller, and the robotic transfer mechanism can operate to move a robotic head 32, and thus, a specimen container, to a specific well 24 (i.e., as determined by the X, Y position for the centerline of the specific well) in the rack 22 and deposit the container therein. In operation, the automated transfer mechanism 30 can operate to pick-up a specimen container, for example, at an entrance location or container pick-up station, transfer the container to, and deposit the container into, an individual well 24 of the detection system. As described further in US 2011/0124028, the automated transfer mechanism may also operate to remove a specimen container determined "positive" for microbial growth, from a specific well 24, and transfer the specimen container to a positive container exit location 16, and/or to transfer a container determined "negative" for microbial growth to a negative container location or waste bin.

Transfer Mechanism and Gripping Mechanism

Figure 3A:
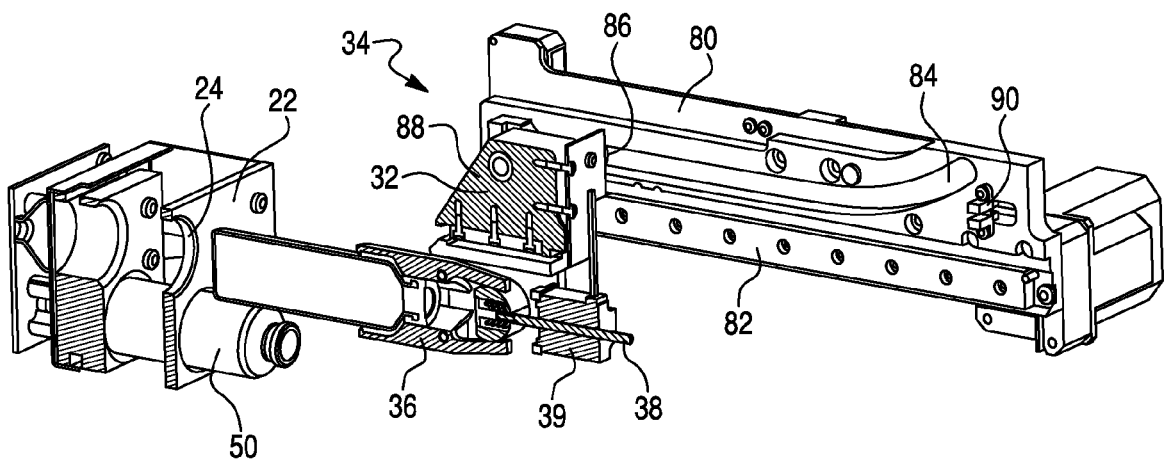
FIGS. 3A-B are perspective views of the pivot plate and robotic head of the automated transfer mechanism shown in FIG. 2. The robotic head is shown with a cross-sectional view of the gripping mechanism and specimen container to reveal the features of the gripping mechanism.
Figure 3B:
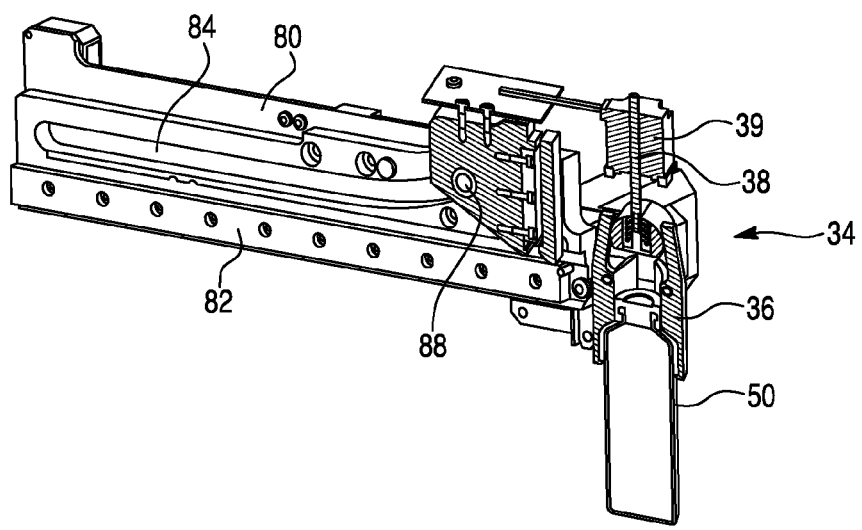

As shown, for example in FIGS. 3A-3B, the illustrated automated detection system 2 includes an automated transfer means or mechanism (e.g., a robotic transfer arm) operable for the transfer of a specimen container within the system. The detection system 2 may receive specimen containers from an automated loading mechanism 20, shown best in FIG. 1. As the containers enter the system at an entrance location or port, the transfer mechanism can picked-up the specimen containers (e.g., at a pick-up station or location) and move them into the detection system 2, as described in greater detail in U.S. 2011/0124028. In accordance with this aspect of the present invention, the transfer mechanism (e.g., a robotic transfer arm_further comprises a container gripping mechanism or gripper, operable to pick-up, or otherwise receive, an individual specimen container 50 and transfer and place that container into an individual well 24 of a the holding structure or rack 22 within the detection system 2. However, as one of skill in the art will appreciate, other designs for the robotic transfer arm and/or gripper mechanism are possible and contemplated in the practice of the present invention.

Specimen containers 50 are typically loaded into the detection system 2 in a vertical orientation (i.e., such that the top or cap portion of the container is up-right). However, as shown best in FIGS. 1-2 and 13-14, the containers 50 are placed or held in a plurality of wells 24 within holding structures or racks 22 in a horizontal orientation (i.e., such that the specimen container is also orientated in a horizontal orientation), and optionally agitated to enhance microorganism growth therein. Accordingly, the automated transfer mechanism must re-orientate the container 50, from a vertical orientation to a horizontal orientation, during the transfer of the container 50 from the loading mechanism 20, or pick-up station, to the wells 24 of the holding structure or racks 22.

In operation, the automated transfer mechanism 30 can operate to transfer or otherwise move, or relocate, a specimen container 50 within the interior chamber 10 of the detection system 2. For example, in one embodiment, the transfer mechanism 30 can transfer a specimen container 50 from a pick-up station or location (e.g., at an entrance location or port) to one of a plurality of holding structures or racks 22. In another embodiment, the transfer mechanism can operate to remove or unload "positive" and "negative" containers from the holding structures or racks 22. This automated unloading mechanism can operate to ensure that once a "positive" or "negative" determination has been made for each specimen container 50, the container 50 is removed from the well 24 of a holding structure or rack 22, making room for another container to be loaded into the detection system 2, thereby increasing system through-put.

In one embodiment, the transfer mechanism 30 can be a robotic transfer arm. In general, any type of robotic transfer arm known in the art can be used. For example, the robotic transfer arm 30 can be a multi-axis robotic arm (for example, a 2-, 3-, 4-, 5-, or 6-axis robotic arm). Furthermore, to facilitate the necessary movements of the transfer mechanism or robotic transfer arm, the interior chamber 10 of the detection system 2, may include one or more supports for the robotic transfer arm. For example, one or more vertical supports and/or one or more horizontal supports may be provided. The transfer mechanism or robotic transfer arm will move, or slide, up and down and across these supports as necessary to access any of the individual wells 24 of the holding structures or racks 22. As previously described, the robotic transfer arm can operate to change the orientation of a specimen container from a vertical orientation (i.e., up-right orientation such that the top or cap of the container is up) to a horizontal orientation (i.e., such that the container 50 is laying on its side), for example, to facilitate in container transfer from a pick-up or loading station to placement within a holding structure and/or agitation assembly.

In one embodiment, the robotic transfer arm is a 2-, or 3-axis robotic arm and will be capable of transferring the container 50 in one or more horizontal axes (for example, the x- and/or z-axes) and optionally a vertical axis (y-axis) to a specific location, such as the container wells 24 described herein. In accordance with this embodiment, a 2-axis robotic arm will allow movement in 2-axes (for example, the x-, and z-axes), whereas a 3-axis robotic arm will allow movement in 3-axes (for example, the x-, y-, and z-axes).

In another embodiment, the 2-, or 3-axis, robotic arm may further employ one or more rotational movements, capable of transferring or moving the specimen container 50 rotationally about one or more axes. This rotational movement may allow the robotic transfer arm to transfer a specimen container 50 from a vertical loading orientation to a horizontal orientation, as described elsewhere herein. For example, the robotic transfer arm may employ a rotational movement to move the specimen container rotationally about or around a horizontal axis. This type of robotic transfer arm would be defined as a 3-, or 4-axis robotic arm. For example, a robotic arm that allows movement in one horizontal axis (the x-axis), one vertical axis (e.g., the y-axis) and one rotational axis would be considered a 3-axis robotic arm. Whereas, a robotic arm that allows movement in two horizontal axes (e.g., the x-, and z-, axes), a vertical axis (the y-axis) and one rotational axis would be considered a 4-axis robotic arm. Similarly, a robotic arm that allows movement in a single horizontal axis (e.g., the x-axis), a vertical axis (the y-axis) and two rotational axes would also be considered a 4-axis robotic arm. In yet another embodiment, the robotic transfer arm 30 can be a 4-, 5-, or 6-axis robotic arm, thereby allowing movement in the x-, y-, and z-axes, as well as rotational movement about, or around, one-axis (i.e., a 4-axis robot), two axes (i.e., a 5-axis robotic arm), or all three horizontal axes (x-, and z-axes) and vertical axes (y-axes) (i.e., a 6-axis robotic arm).

One possible design possibility for the automated transfer mechanism or robotic transfer arm is shown in FIGS. 1-3B. As shown in FIGS. 1-3B, the robotic transfer arm 30 will include one or more horizontal support structures 40, one or more vertical support structures 42, and a robotic head 32 that will include one or more features or devices (i.e., a gripping mechanism) 34 to pick-up, grip and/or hold a specimen container 50. The robotic head 32 can be supported by, coupled to, and/or attached to one of the horizontal supports and/or vertical supports. For example, in one embodiment, as shown in FIGS. 1-3B, the robotic transfer arm 30 comprises a lower horizontal support structure 40 and a single vertical support structure 42. Although, not shown, as one of skill in the art would appreciate an upper horizontal support structure, or other similar means can be used to further support or guide the vertical support structure. In general, any known means in the art can be used to move the robotic head 32 up and down the vertical support rail 42 (as represented by arrow 46 (see FIG. 2)), and move the vertical support rail 42 back-and-forth along the horizontal support structure(s) 40 (as represented by arrow 47 (see FIG. 2)). For example, as shown in FIG. 2, the robotic transfer arm 30 may further comprises a vertical drive motor 60 and vertical drive belt or timing belt 62 that will operate to transfer or move the robotic head 30 up and down (arrow 46) the vertical support rail 42 to transfer or move a container 50 along (i.e., up and down) a vertical axis (i.e., the y-axis). The vertical support structure 42 may further comprise a vertical guide rail 64 and a robotic head support block or carriage 66, as shown in FIG. 2. Accordingly, the vertical support structure 42, vertical guide rail 64, vertical drive motor 60 and vertical drive belt or timing belt 62 allow the robotic transfer arm 30 to move or transfer the robotic head support block or carriage 66, and thus, the robotic head 32 and a specimen container 50 along the y-axis. Likewise, also as shown in FIG. 2, the robotic transfer arm 30 may further comprise a first horizontal drive motor (not shown), first horizontal drive belt or timing belt 72 and horizontal guide rail 74 that will operate to move the vertical support structure 42 back-and-forth (i.e., from left-to-right and/or from right-to-left) along the horizontal guide rail 74, and thus, along a first horizontal axis (i.e., the x-axis) within the housing 4 of the detection system 2 (see arrow 47)). Accordingly, the horizontal support structure(s) 40, first horizontal drive motor (not shown), first horizontal drive belt 72 and horizontal guide rail 74 allow the robotic transfer arm 30 to move or transfer a specimen container 50 along the x-axis. Applicants have found that by including a vertical support that is movable along a horizontal axis allows for an increased capacity within the detection system, as the robotic transfer arm is movable over an increased area within the instrument. Furthermore, Applicants believe a robotic transfer arm having a movable vertical support may provide a more reliable robot transfer arm.

As shown best in FIGS. 1-3B, the automated transfer mechanism or robotic transfer arm 30 may further comprise a linear or horizontal slide 82 and pivot plate 80. As shown, for example in FIGS. 1-3B, the linear or horizontal slide 82 supports the robotic head 32 and gripper mechanism 34. The linear or horizontal slide 82 and robotic head 32 may be supported by, coupled to, and/or attached to, a robotic head support block 66 and vertical guide rail 64 (previously described). In accordance with this embodiment, the linear or horizontal slide 82 can be moved up and down (see FIG. 2, arrow 46) along a vertical axis (i.e., the y-axis), via the a robotic head support block 66 and vertical guide rail 64, to move or transfer the robotic head 32 and/or specimen container 50 up and down within the housing 4 of the detection system 4 (i.e., along the vertical axis (y-axis)). As shown in FIGS. 1-3B, the linear or horizontal slide 82 may further comprises a pivot plate 80 comprising a guide rail 82, a pivot slot 84 and pivot slot cam follower 86 operable to allow the robotic head 32 to slide or moved along the linear or horizontal slide 82, from front-to-back or from back-to-front (see FIG. 2, arrow 48), to transfer or move a container 50 along a second horizontal axis (i.e., the z-axis). In accordance with this embodiment, a second horizontal drive motor or horizontal slide motor (not shown) and a slide drive or timing belt (not shown) can be used to move the robotic head 32 along the z-axis. Accordingly, the linear or horizontal slide 82, the horizontal slide motor and slide belt, allows the robotic head 32 to move or transfer a specimen container 50 along the z-axis. As known in the art, one or more sensors (see, e.g., 90 in FIG. 3A) can be used to indicate the initial or home position of the robotic head 32 on the linear or horizontal slide 82.

As shown in FIGS. 1-3B, as the robotic head 32 is moved along the linear or horizontal slide 82, pivot plate 80 and pivot plate guide rail 84, the pivot slot 84 and pivot slot cam follower 86 rotate the pivot carriage 88 about or around a horizontal axis (i.e., the x-axis), and thus, rotates the robotic head 32 from a horizontal orientation (as shown in FIG. 3A) to a vertical orientation (as shown in FIG. 3B), or vice versa. As described elsewhere herein, the transfer of a container 50 from a vertical entry orientation to a horizontal orientation may be necessary for depositing or placing the container in a horizontally orientated well 24 of the holding structure or rack 22. Accordingly, the pivot plate 80, pivot slot 84 and pivot carriage 88 allow the robotic head 32 to re-orientate a specimen container 50 from a vertical orientation, as loaded into the detection system 2, to a horizontal orientation, thereby allowing a specimen container 50 to be transferred from an automated loading mechanism 20, or pick-up station, to a well 24 in a holding structure or rack 22 As shown in FIG. 1 the automated transfer mechanism may also comprise one or more cable management chains 92, for cable management within the detection system 2, and a circuit board 94 for controlling the robotic transfer mechanism. In yet another embodiment, the robotic transfer arm 30 may further comprise a brake mechanism 96 that can operate to brake the vertical drive belt 62, thereby preventing it from falling to the bottom of the instrument (e.g., due to a power outage).

The robotic transfer arm 30 may further comprise a gripping mechanism 34 to pick-up, grip or otherwise hold a specimen container 50. As shown, for example in FIGS. 1-3B, the gripping mechanism 34 may comprise at least two gripping fingers 36. In other embodiments the gripping mechanism may comprise from 2 to 6 gripping fingers, from 2 to 4 gripping fingers, 3 gripping fingers or 4 gripping fingers. In one possible embodiment, the gripping mechanism 34 may further comprise a linear actuator 38 and a linear actuator motor 39 which can operate to move the linear actuator to open and close the gripper fingers 36. In operation, as is well known in the art, the actuator motor 39 can be used to move the linear actuator 38 of the gripper mechanism 34 thereby moving the gripper fingers 36. For example, the linear actuator can be moved in a first direction (e.g., toward the motor) to close the fingers and grip the container 50. Conversely, the linear actuator can be moved in a second direction (e.g., away from the motor) to open the gripper fingers and release the container 50. Applicants have unexpectedly found that the use of one or more gripping fingers 36 allows the gripping mechanism 34 to accommodate (i.e., pick-up and/or hold) a large variety of different specimen containers 50. Moreover, Applicants have found that by using gripper fingers 36 that extend from about one-quarter (¼) to about one-half (½) the length of the specimen container 50, the gripper fingers will accommodate (i.e., pick-up and/or hold) a number of well-known containers (e.g., long neck blood culture bottles) in the art.

Figure 4:
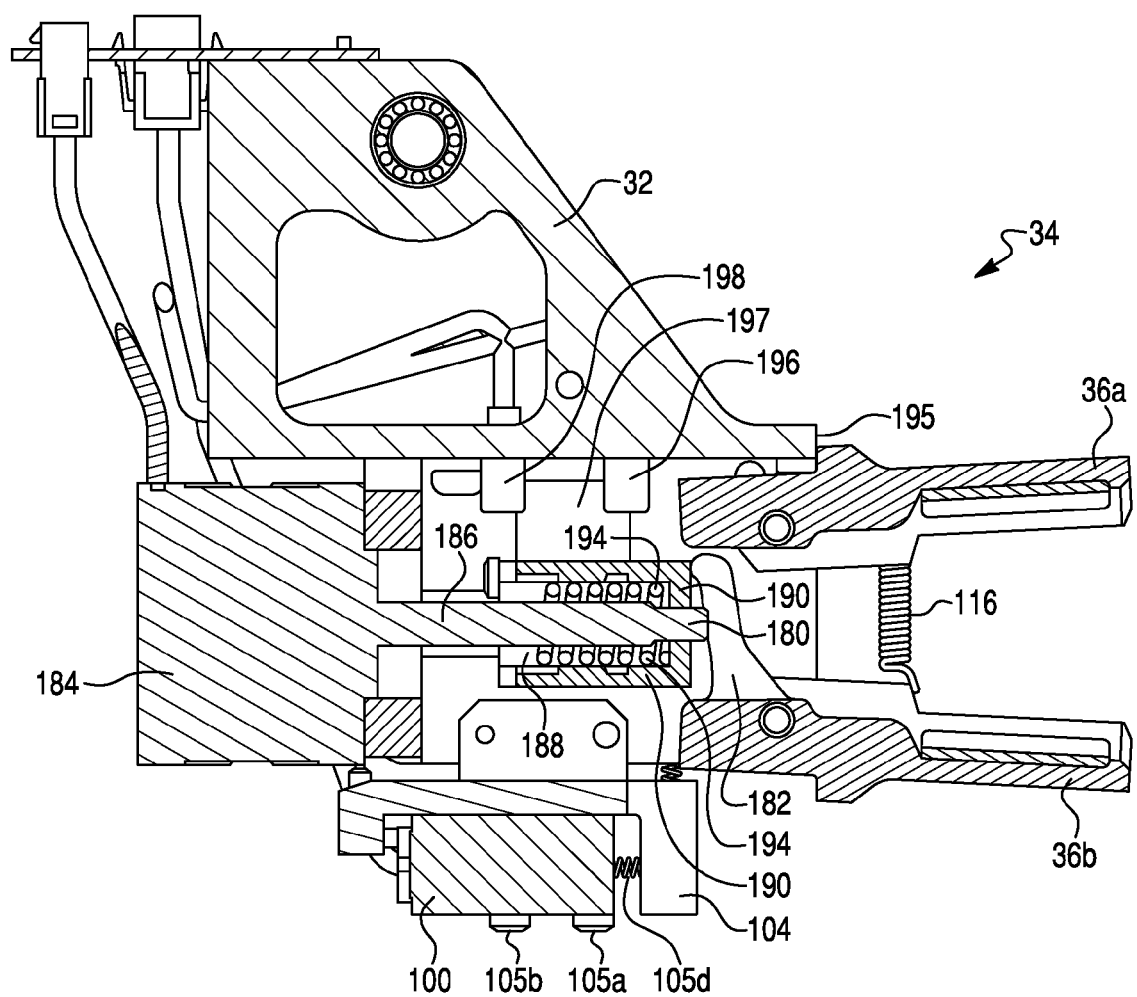
FIG. 4 is a cross-sectional view of a robotic head and gripping mechanism, in accordance with an alternative embodiment of the present invention.

Another embodiment of the gripping mechanism is illustrated in FIG. 4. As shown in FIG. 4, the gripper fingers 36a, 36b rotate on a shaft to close around a specimen container (not shown) to grip and securely hold the container. In accordance with this embodiment, two extension springs 116 provide the force to grip and retain the container in the gripper fingers 36a, 36b. The use of extension springs 116 to provide the gripping force ensures that a container is not dropped in the event of a power failure. The extension springs 116 require no electrical power to maintain the grip on the container. Furthermore, the use of two extension springs 116 provides redundancy to the gripper in the event that a spring breaks or becomes dislodged from its mounting point.

To open the gripper, the force of the extension springs 116 must be overcome. As shown in FIG. 4, a sliding cam block 190 applies the force to open the gripper fingers 36a, 36b. The gripper fingers 36a, 36b are configured with levers 182 that the sliding cam block 190 engage. A linear actuator motor 184 drives a leadscrew 186, which in turn drives a nut 188, the nut transfers the load to a spring 194 that in turn moves the sliding cam block 190 towards the levers 182. The nut 188 is translated along the length of the leadscrew 186 by the rotary motion provided by the motor 184. The nut 188 is constrained from rotating by retaining it within a recessed pocket of a sliding cam block 190. The sliding cam block 190 may have protrusions 192 (see FIGS. 5A-6A) that engage the gripper housing that prevent its rotation so that it is constrained to move in a linear motion. Also as shown, two sensors, a first or open sensor 196 detects when the gripper fingers are in the "open" position and a second or closed sensor 198 detects when the gripper fingers 36a, 36b are in the "closed" position. In one embodiment, as shown in FIG. 4, the open sensor 196 and closed sensor 198 indicate detection of the "open" and "closed" positions, respectively, when a flag 197 triggers detection.

In operation, force applied by the nut 188 is transmitted through a spring 194. The stiffness of the spring 194 is such that it will not compress while the gripper extension springs 116 are being opened. When the grippers reach the fully open position, they engage a hard stop 195 and cease to rotate open. A first sensor 196 detects that the gripper fingers are fully open, and the linear actuator motor 184 is stopped. The motor 184 will not stop immediately when the gripper open sensor 196 is triggered. For a short time after the sensor is triggered, the leadscrew 186 may continue to move the nut 188 forward causing the spring 194 to compress or deflect. The compression of the spring 194 prevents the nut 188 from becoming locked on the leadscrew 186.

As described elsewhere herein, the automated transfer mechanism or robotic transfer arm 30 and gripper mechanism 32 can be placed under the control of a system controller (not shown) and programmed for specimen container 50 management (e.g., pick-up, transfer, placement and/or container removal) within the detection system 2. In one embodiment, the controller determines the X and Y positions of one or more individual specimen container wells 24 (or the X and Y positions of the centerline) and provides the X and Y positions to the robotic transfer mechanism for proper placement, or deposit, of a specimen container 50 into an individual well 24.

Laser Alignment Device and Alignment Tool

In one embodiment, the present invention is directed to an alignment system comprising a laser alignment device operable to provide precise locational coordinates for alignment of said robotic transfer mechanism relative to the holding structure and one or more holding or receiving wells, and thereby allowing for proper placement or loading and proper unloading of specimen containers into or from said one or more holding or receiving wells. In operation, the laser alignment device can be used to detect (i.e., is operable to detect) one or more fiducials on the holding structure, and thereby determine an initial, or home position for the robotic transfer mechanism relative to the holding structure (e.g., to determine the initial, or home position for the centerline of the gripping device relative to the holding structure). A controller can then be used to determine, or calculate, the X and Y positions of each individual well (e.g., the X and Y positions for the centerline of each individual well) relative to the initial, or home, position of the robotic transfer mechanism, and thereby ensure accurate placement, or deposit, of a container into an individual well. In another embodiment, the present invention is direct to an alignment tool that can be attached to the robotic head and gripping device and to a method of establishing the proper alignment of the laser alignment device relative to the robotic head and gripping device (e.g., the centerline of the gripping device). Applicants have found that proper alignment of the laser alignment device and gripping device can assist with establishment of proper alignment of the robotic transfer mechanism, and thus, the gripping mechanism relative to the individual wells in a holding structure or rack. In other words, by establishing proper alignment of the laser alignment device with the gripping mechanism (e.g., the centerline of the gripping mechanism), the laser alignment device can be used to establish and/or maintain proper alignment of the gripping mechanism with one or more fiducials on the holding structure. The controller can them be used to determine, or calculate, the X and Y positions of each individual well (e.g., the centerline of individual wells), as previously described.

Referring now to the Figures, FIGS. 5A-7 show a robotic head 32 and gripping mechanism (or gripper) 34 in accordance with one embodiment of the present invention. As shown, and as previously described, the robotic head 32 comprises a gripping mechanism 34 having 2 opposed gripping finger 36a and 36b. Also, as previously described, the robotic head 32 is attached to a pivot plate 80 and linear or horizontal slide 82 (see, e.g., FIGS. 2-3B), which allows for movement of the robotic head along the z-axis and rotation about the x-axis, as described above. The robotic head further includes a laser alignment device 100, which can transmit a laser beam 102 (see, e.g., FIG. 5B) under the control of a controller device through laser cable 106. As received from the manufacturer, the angular tolerance of the laser beam projection is typically ±3° relative to its case mounting surface. To account for this manufacturing variation of the laser, the laser can be mounted to an adjustable base 104. The laser beam 102 projects from the front of the laser device 100 and detects the reflection of the beam off of a surface, for example the holding structure or rack. Typically, the laser beam 102 can be used to detect the edge of a surface (or the edge of a fiducial, as described herein) and is repeatable within 0.3 mm. The laser beam is adjusted to a fixed location relative to the centerline of the gripper with the use of an alignment tool, as described in further detail elsewhere herein. The alignment tool comprises a support arm 54, which supports a fiducial plate 56 and an alignment fiducial 58 (see FIGS. 6A-6B), and optionally removable positioning piece 240 (see FIGS. 8A-8C), and is precisely and removably attached to the gripper using one or more pins. In use, the distance from the laser to the alignment tool is the same as the distance from the laser to the fiducials located on the holding structure or racks.

The adjustable laser alignment device 100 can be attached to the robotic head 34 using the adjustable base 104, which further comprises a first adjustment mechanism 105a-d for adjustment of the laser beam 102 along the x-axis and a second adjustment mechanism 108 for adjustment of the laser beam 102 along the y-axis. The first and second adjustment mechanisms 105, 108 can be independently adjusted and locked into position once properly adjusted. The first adjustment mechanism 105 includes a pivot screw 105*c* (see FIG. 6A), about which the laser can rotate, and two locking screws 105*a*, 105*b*, which allow the laser to be adjusted along the x-axis, and which can be locked to secure the laser once properly aligned. The first adjustment mechanism 105 further includes an adjustment screw 107 that facilitates rotation of the laser about the pivot screw 105*c*. In operation when the adjustment screw 107 is tightened the laser beam 102 moves from left to right in x-axis. The first adjustment mechanism also includes a spring 105*d* that provides a return force to move the laser beam 102 from right to left along the x-axis when the adjustment screw 107 is untightened.

The second adjustment mechanism 108*a-c* includes a pivot pin 108*b*, about which the laser can rotate, and a locking screws 108*a*, which allow the laser to be adjusted in the y-axis, and which can be locked to secure the laser once properly aligned. The second adjustment mechanism 108*a-c* further includes an adjustment screw 109 that facilitates rotation of the laser about the pivot pin 108*b*. In operation when the adjustment screw 109 is tightened the laser beam 102 moves in the y-axis from a lower location to a higher location on the y-axis. The second adjustment mechanism also includes at least one spring 108*c* that provides a return force to move the laser beam 102 from a higher location to a lower location on the y-axis when the adjustment screw 109 is untightened.

The first and second adjustment mechanisms 105*a-d*, 108*a-c* can be used to align the adjustable laser device 100 as shown in FIG. 21. These adjustment mechanisms 105, 108 allow a user or technician to properly align the laser device 100 relative to fiducials located on the alignment tool and/or on the holding structure or rack, as described elsewhere herein. Once properly aligned, and knowing the precise distance between the laser beam 102 and the centerline 110 of the gipping mechanism (i.e., the precise distance in the X and Y directions) (see, e.g., FIG. 7) the precise X and Y coordinates of the centerline 110 of the gripping mechanism 34 can be determined by the controller. Next, the laser alignment device can be used to detect one or more fiducials located on the holding structure or rack 22, and used by the controller to determine the initial or home position of the robotic transfer mechanism, and thus, gripping mechanism relative to the holding structure or rack. Knowing the precise initial, or home position, of the robotic transfer mechanism or gripping mechanism relative to the holding structure or racks, allows the controller to determine, or calculate, the precise X and Y positions of each individual well 24 (or more specifically, the X and Y positions for the centerline of each individual wells 24). The system controller can then precisely coordinate the movement of the robotic transfer mechanism, and thus, gripping mechanism, for proper alignment with the holding or receiving wells 24, and thus, proper loading and unloading of a specimen container, into or from, a specific well 24 in the holding structure or rack 22.

In one embodiment, as shown in FIGS. 9A-9B the holding structure or rack 22 comprises one or more square fiducials 26. In operation, these fiducials 26 on the holding structure or rack 22 can be used to determine, or set the initial or home position of the robotic transfer mechanism relative to the holding structure or racks 22. Furthermore, as noted herein, knowing the initial or home position of the robotic transfer mechanism relative to the holding structures allows for determination of the X and Y positions for the centerline 28 of each individual well 24. As shown in FIGS. 9A-9B, the fiducial 26 may comprise a square shaped hole in the holding structure or rack 22. In accordance with this embodiment, the laser device 100 is used to find two edges (a first edge in a y-axis, and a second edge in a x-axis) of the square fiducial 26. By aligning the laser beam 102 of the laser alignment device 100 to the x-, and y-edges of the square fiducials 26, the precise X and Y coordinates of the centerline 28 of each individual well 24 in the holding structure or rack 22 can be precisely determined (as noted above), thereby allowing for alignment of the gripping mechanism 34 with individual wells 24. In one embodiment, the centerline of the gripping mechanism can be aligned with, or relative to, the centerline of the individual wells 24 (i.e., co-axial alignment of the centerline of the gripping mechanism with the centerline of the individual wells).

In another embodiment, the invention is directed to a method for alignment of the laser alignment device 100 with one or more square fiducials 26 located in an alignment tool and/or located on a holding structure or rack 22. In accordance with this embodiment, the laser alignment device 100 can be positioned such that the laser beam 102 is aligned with a target as shown by the sequence of adjustments provided in FIG. 21.

Figure 6A:
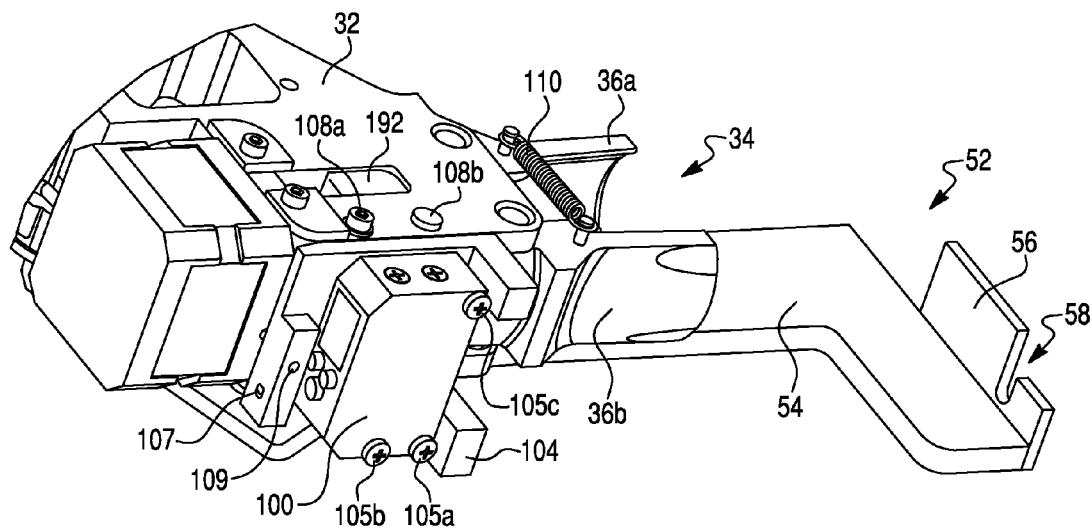
FIGS. 6A-6B show an alignment tool attached to the robotic head and gripping mechanism, in accordance with one embodiment of the present invention.
Figure 6B:
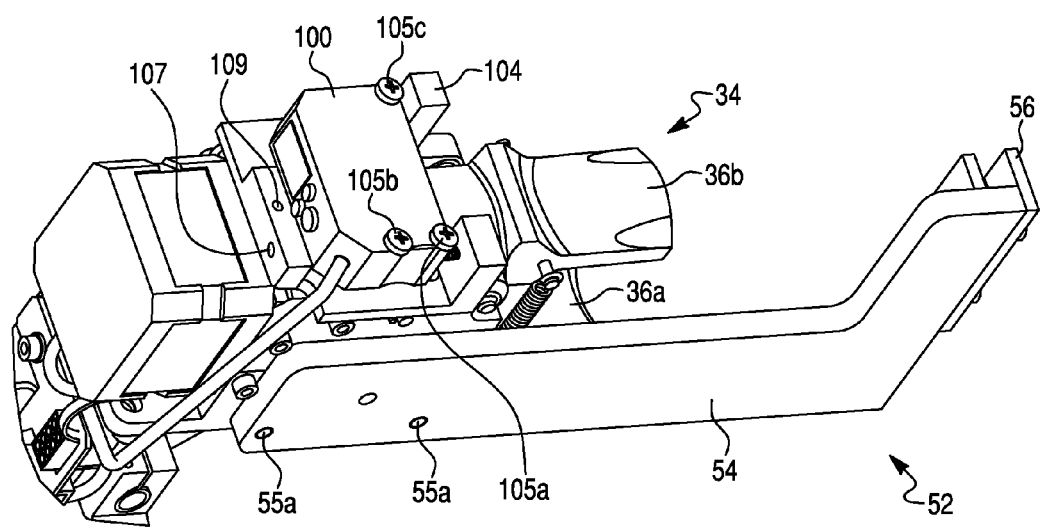
Figure 7:
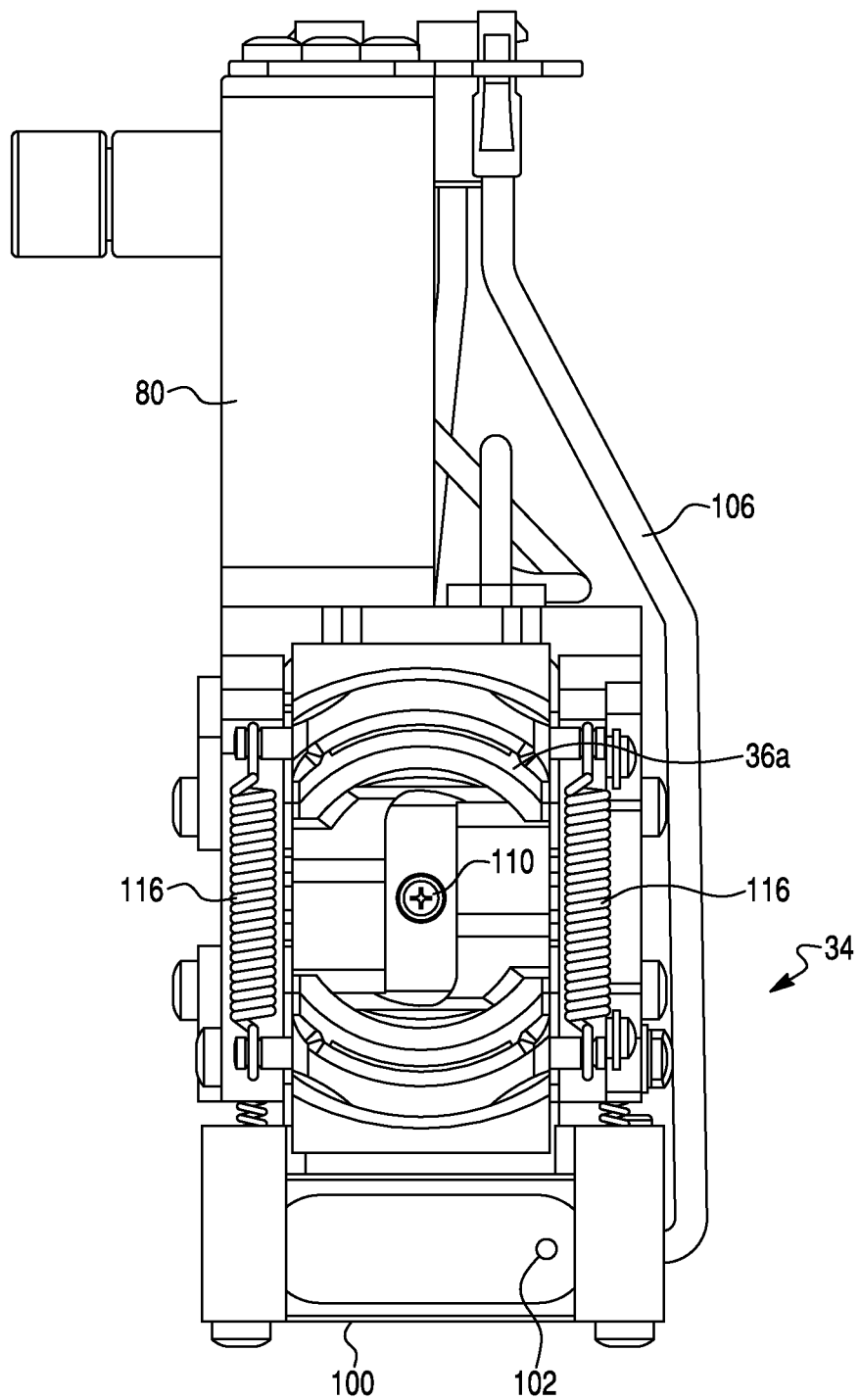
FIG. 7 is a front perspective view of the robotic head and gripping member shown in FIGS. 5A-5B.

As noted in FIG. 21, the alignment system of the present invention may include an alignment tool 52. As shown in FIGS. 6A-6B, the alignment tool 52 comprises a support arm 54, which supports a fiducial plate 56 and an alignment fiducial 58. In operation, the alignment tool 52 can be attached to the robotic head 32 using a pair of pins 55*a* (FIG. 6B) on the alignment tool 52 that mate with a pair of pin holes 55*b* (FIGS. 5A-5B) located on the robotic head 32. In one embodiment, the support arm 54 of the alignment tool 52 comprises a length (L) that when attached to the robotic head 32 allows the alignment fiducial 58 of the tool to be spaced the same distance (i.e., a distance Z) from the robotic head 32 as the fiducials 26 of the holding structure 22 are spaced from the robotic head 32. In other words, distance Z is both the distance from the laser 100 to the tool alignment fiducial 58, as well as the distance from the laser 100 to the square fiducials 26 of the holding structure or rack 22, thereby allowing the alignment tool 52 to be used to establishing and/or maintaining proper alignment of the robotic head 32 and gripping mechanism relative to the holding structure 22 and wells 24 (i.e., co-axial alignment of the gripping mechanism and the wells 24 of the holding structure 22).

In operation, the laser alignment device 100 can be adjusted relative to the alignment fiducial 58 of the alignment tool 52, to ensure proper alignment of the laser alignment device 100 relative to the robotic transfer mechanism, and thus, the gripping mechanism. Once properly aligned, the alignment tool 52 can be removed and the laser alignment device 100 can be used to establish proper alignment of the robotic transfer mechanism relative to the holding structure or racks 22, or more specifically, to the edges of the alignment fiducial (i.e., a first edge in a y-axis, and a second edge in a x-axis), as previously described. Once properly aligned, the controller can then precisely calculate the precise X and Y positions of each individual well 24 in the holding structures or racks 22. Knowing the precise location (i.e., x-, y-coordinates) of each individual well 22 relative to the fiducials 26 of the holding structure 22 allows the controller to precisely control the movement of the robotic head 32 for transfer to, and proper loading and unloading of a specimen container, into or from, a specific well 24 in the holding structure or rack 22. In still another embodiment, the identification of the fiducials 26 of a specific holding structure or rack 22 communicates to the controller that a holding structure or rack 22 is present, thus ensuring a holding structure or rack 22 is present before the controller places or loads a container into the holding structure or rack 22.

Figure 8A:
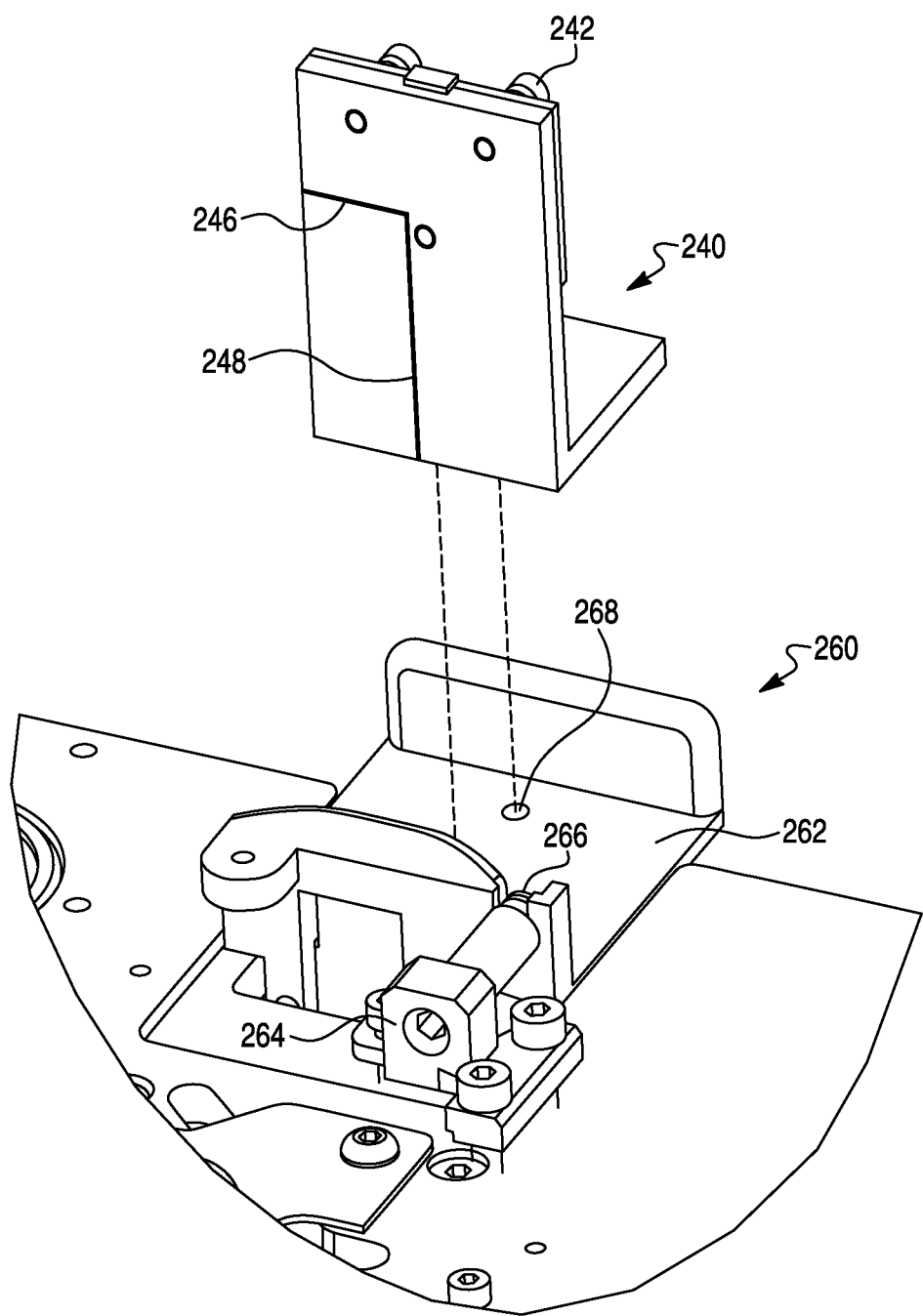
FIGS. 8A-8C are perspective views showing the robotic head and gripping mechanisms of FIGS. 5-7 relative to a container pick-up station, in accordance with one embodiment of the present invention.
Figure 8B:
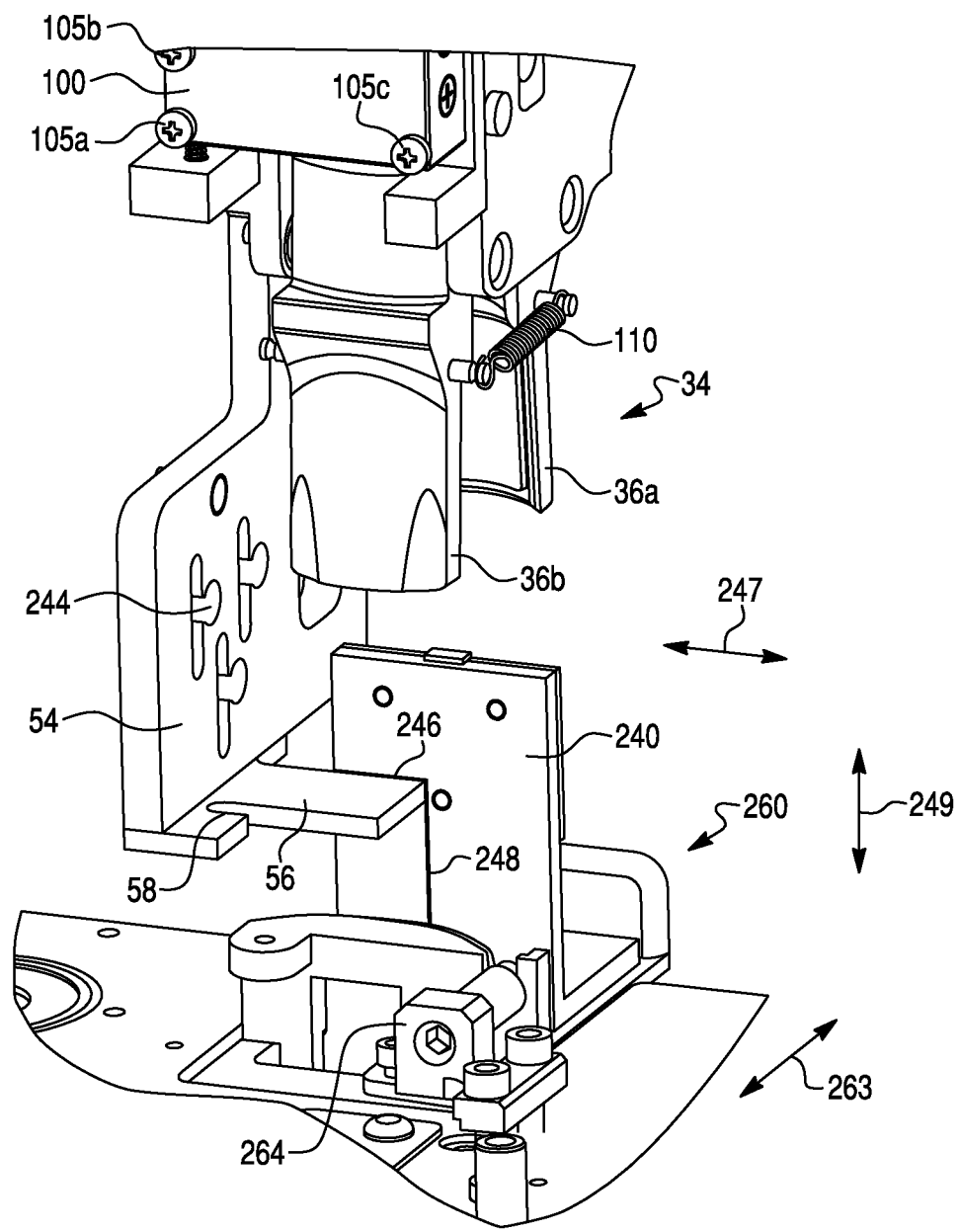
Figure 8C:
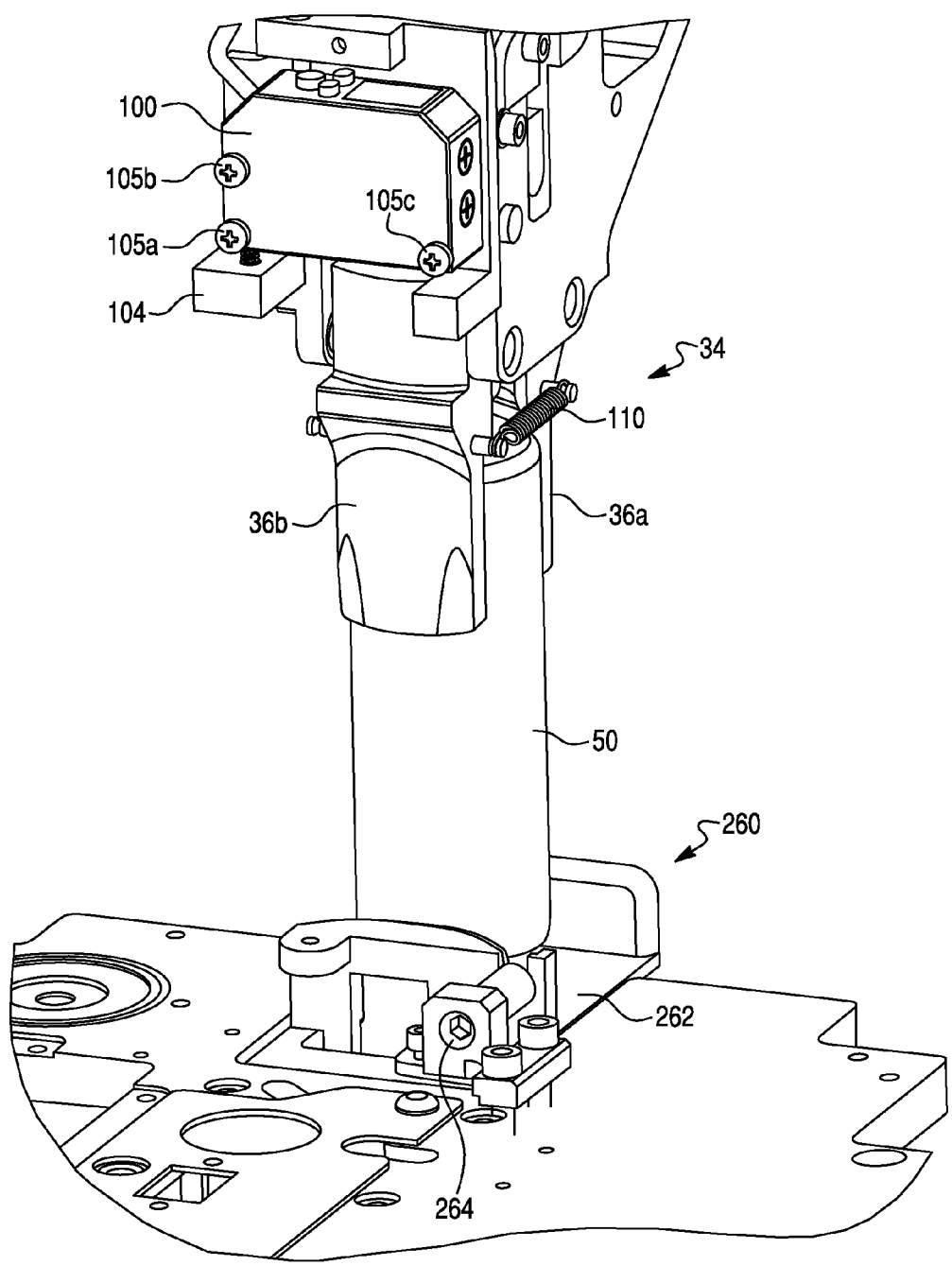
Figure 10A:
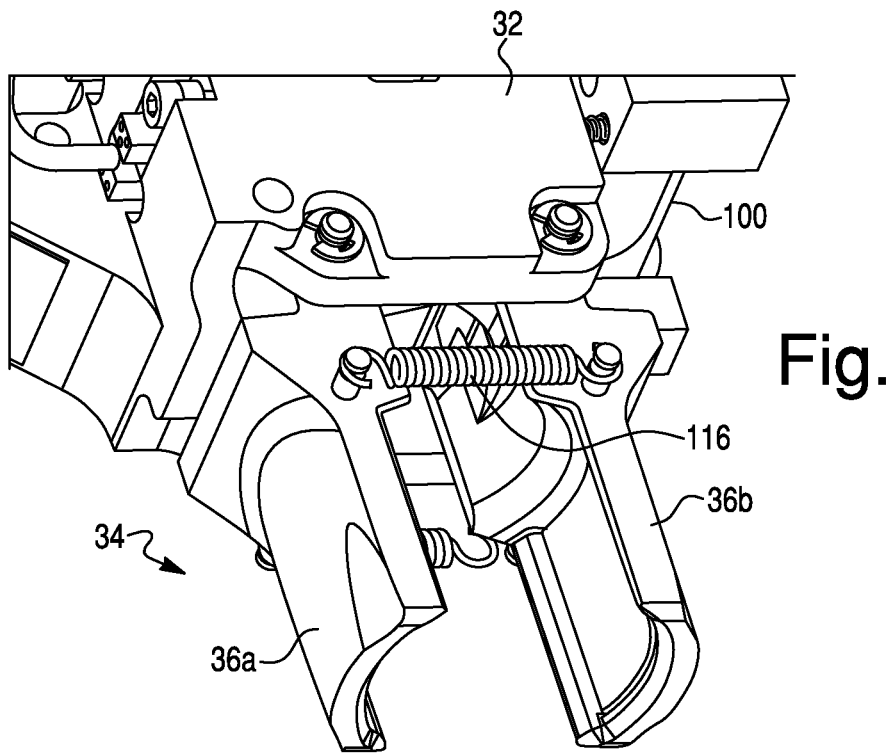
FIG. 10A-10B are perspective close-up views showing the gripping mechanism and gripping fingers of FIGS. 5A-7, in accordance with one embodiment of the present invention.
Figure 10B:
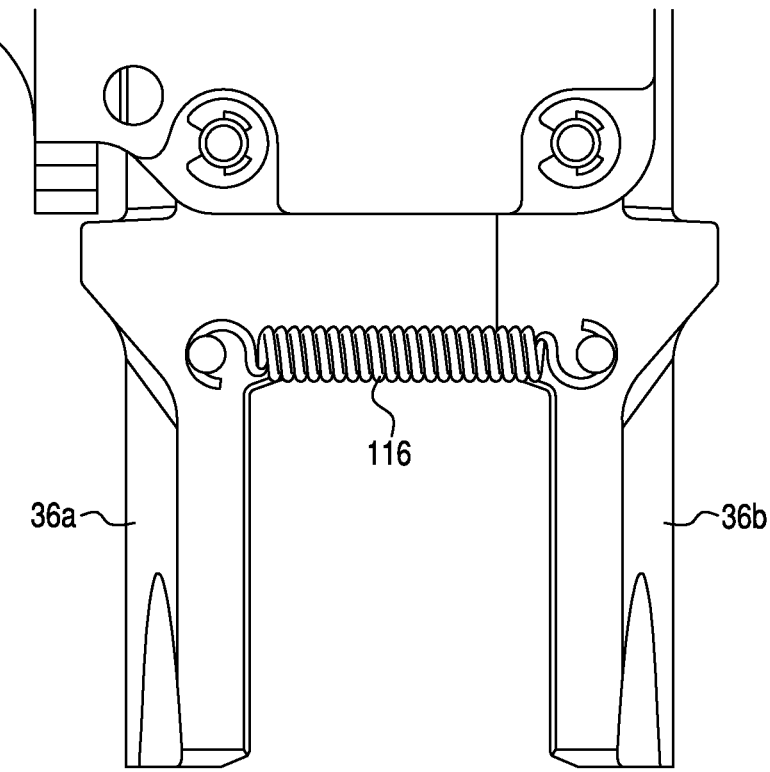
Figure 11:
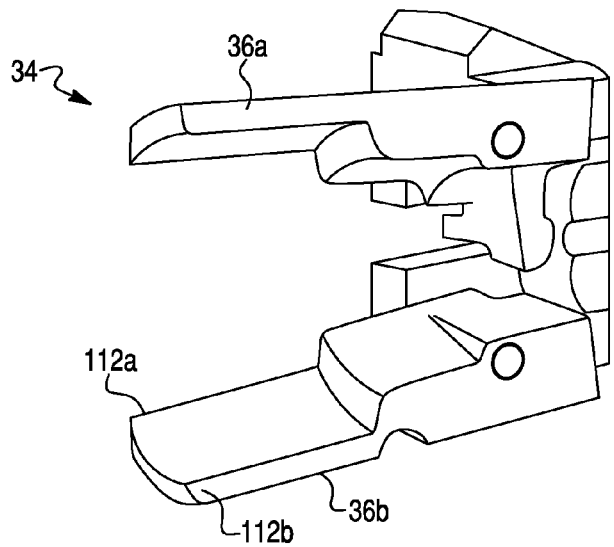
FIG. 11 is a solid-sectional view showing the gripping mechanism and gripping fingers of Fingers 5A-5B and FIGS. 9-10, in accordance with one embodiment of the present invention.
Figure 12A:
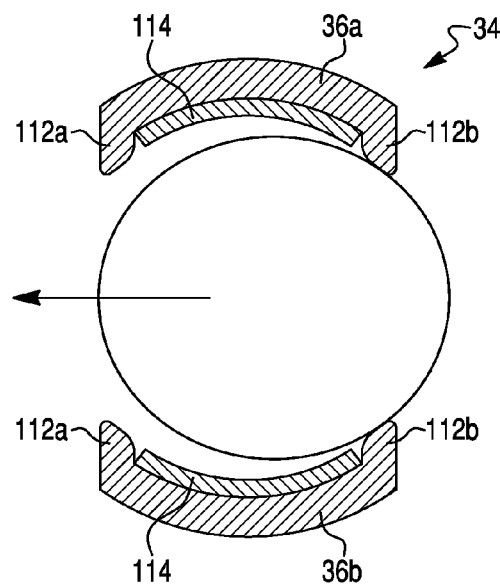
FIG. 12A-B are front cross-sectional views of the gripping fingers shown in FIGS. 4-7 and 10A-11.
Figure 12B:
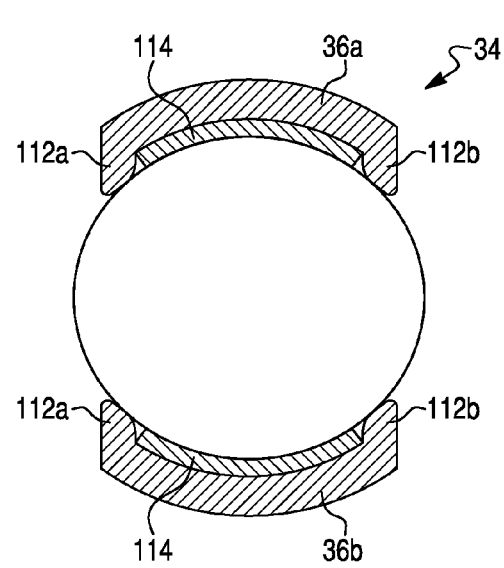

In another embodiment, the alignment tool 52 may further comprise a removable positioning piece 240 operable for proper co-axial alignment of the gripping mechanism 34 with a pick-up station 260, and thus, a specimen container 50 located therein, as shown in FIGS. 8A-8C. The removable positioning piece 240 can be attached to the alignment tool using attachment pins 242 that mate with a pair of pin engagement slots 244 on the support arm 54 of the alignment tool 52, thereby establishing proper alignment of the removable positioning piece 240 with the pick-up station 260. The removable positioning piece 240 further comprises a horizontal indicator line 246 and a vertical indicator line 248 useful, or operable, to establish proper alignment of the gripping mechanism 34 in the x-axis (as represented by arrow 247 (see FIG. 8B)), and y-axis (as represented by arrow 249 (see FIG. 8B)) relative to the pick-up station 260, and thus, a specimen container 50 contained therein (see, e.g., FIG. 8C). The pick-up station 260 may further comprise a pick-up station adjustment screw 264. The adjustment screw 264 can be adjusted to position the working end 266 of the adjustment screw and thereby the base plate 262 of the pick-up station 260 in the z-axis (as represented by arrow 263 (see FIG. 8B)) relative to the gripping mechanism 34 so that a specimen container 50 is properly picked-up from the pick-up station 260. The removable positioning piece 240 and the adjustment screw 264 allows for proper alignment in the x-, y-axis of the gripping mechanism 34, and proper alignment of a specimen container in the z-axis, to establish and/or maintain proper co-axial alignment of the centerline of the gripping mechanism 34 with a specimen container 50 located within the pick-up station 260 (i.e., to establish co-axial alignment of the centerline of a specimen container contained within the pick-up station with the centerline of the gripping mechanism).

In operation, the removable positioning piece 240 can be placed within the pick-up station 260 and centered therein using pins (not shown) that mate with pin holes 268 located within the base plate 262 of the pick-up station 260. Once properly centered, the horizontal and vertical indicator lines 246, 248 of the removable positioning piece 240 can be used for alignment of the fiducial plate 56, and thereby the gripping mechanism 34, relative to the pick-up station 260, as shown in FIG. 8B. First, the robotic transfer mechanism, and the gripping mechanism 34, are adjusted in the x-axis using the horizontal axis motor, until the leading edge of the fiducial plate 56 aligns with the vertical indicator line 248, thereby establishing proper alignment of gripping mechanism 34 in the x-axis relative to the pick-up station 260 (see FIG. 8A). Next, the robotic transfer mechanism, and gripping mechanism 34, are adjusted in the y-axis using the vertical axis motor, until the top edge of the fiducial plate 56 is aligned vertically relative to the horizontal indicator line 246 thereby setting, in the y-axis, the proper spacing, or height, between the gripping mechanism 34 and the pick-up station 260 (again, see FIG. 8B). Setting the proper vertical spacing, or height, allows for consistent and secure gripping of a specimen container 50, as shown in FIG. 8C.

The present invention is further directed to a method for establishing proper alignment of a robotic transfer mechanism, said transfer mechanism having a robotic head, a gripping mechanism for gripping a specimen container, and an alignment laser, the method comprising the following sequential steps: (a) attaching an alignment tool to the robotic head; (b) aligning the laser alignment device relative to the square fiducial of the alignment tool; (c) adjust the laser alignment device to move the laser beam horizontally (i.e., in the x-axis) towards the left edge of the square fiducial until a sensor LED indicates that the left edge of the square fiducial is detected (i.e., when the LED sensor illuminates); (d) locking down the x-axis alignment screws (i.e., horizontal alignment screws); (e) adjusting the laser device to move the laser beam vertically (i.e., in the y-axis) towards the bottom edge of the square fiducial until the sensor LED indicates the bottom edge of the square fiducial is detected (i.e., when the LED sensor illuminates); and (f) lock down the y-axis alignment screw (i.e., the vertical alignment screw). Once the left edge, and bottom edge, of the alignment tool fiducial have been detected, the laser alignment device is properly aligned relative to the robotic transfer mechanism, or more specifically, to the centerline of the gripping mechanism.

Gripping Mechanism or Device

As one of skill in the art would readily appreciate, proper alignment of a specimen container with the gripping mechanism is required for precise alignment of the gripping mechanism relative to the container, for proper transfer to, and proper loading and unloading of a specimen container, into or from, a well of the holding structure or rack. The present invention is also directed to a gripping mechanism having at least 2 gripping fingers, wherein said gripping fingers define a gripping cavity operable to securely grip and/or hold a specimen container. The gripping cavity further comprises a centerline, along which a specimen container can be properly centered (i.e., co-axial alignment of the gripping mechanism and the specimen container) using the at least two gripping fingers, as described herein below. In other embodiments the gripping mechanism may comprise from 2 to 6 gripping fingers, from 2 to 4 gripping fingers, 3 gripping fingers or 4 gripping fingers.

The gripper fingers employ the use of both hard and soft gripping surfaces. The inventors have surprisingly found that the use of dual gripping materials corrects for and stabilizes the horizontal alignment of specimen containers relative to the robotic head of the robotic transfer mechanism. In a situation where the specimen container is not properly aligned with the centerline of the gripping mechanism as the gripper fingers close, the hard gripping surface will contact the bottle first, forcing the bottle to slide to the centerline of the gripping mechanism. As the gripping fingers continue to close the specimen container is centered. Once the container is centered, the soft gripping surface contacts the specimen container and the higher friction provided by the soft gripping surfaces securely holds the specimen container along the centerline of the gripper. The hard surfaces of the gripping mechanism in contact with the specimen container, further ensures that the container cannot rotate within the gripper in a side-to-side manner, as described in more detail elsewhere herein.

As shown in FIGS. 5A-7 and 10-12B, the gripping mechanism 34 of the present invention comprises 2 opposable semi-circular shaped gripping fingers 36a, 26b. The use of semi-circular shaped gripping fingers 36a, 36b allow for optimal gripping of a specimen container having a semi-circular, or circular shaped cross-section, such as a blood culture bottle. Also, as shown best in FIG. 7, the gripping fingers defining a gripping cavity and a gripping centerline 110.

The gripping mechanism will also include a means for closure of the gripping fingers to securely pick-up, grab, or otherwise hold a specimen container. The gripping means comprises a gripping motor, a threaded screw, first and second gripping actuators, and a spring. In operation, the gripping motor will drive a screw into first and second actuators. The threaded screw, will push the first and second actuators, which are attached to the gripping fingers, thereby moving the gripping fingers to an "open" position such that the gripping mechanism can accept a specimen container. To "grip" the specimen container the motor reverses the screw thereby allowing the spring to pull the gripping fingers to a closed position around the specimen container.

As shown in FIG. 10-12B, each of the opposable gripping fingers 36a, 36b comprises a hard semi-circular gripping surface, each also having an opposable pair of angled alignment nodes 112a, 112b, with a first angled node 112a at a first end of the gripping finger and a second angled gripping node 112b at a second end of the gripping fingers 36a and 36b. Typically, the hard semi-circular gripping surface is a metal, such as aluminum. In one embodiment, the angle first and second alignment nodes 112a, 112b create hard surface areas that force a container to slide to the centerline of the gripping mechanism as the gripping mechanism is closed. Also as shown in FIGS. 10-12B, each gripping finger further comprises a soft gripping pad 114 or surface located at the center of the gripping finger 36a and 36b. The soft gripping pad 114 may comprise any known soft, or elastomeric material known in the art and which provides friction between the gripping pad and container, thereby securely holding the container. In one embodiment, the elastomer can be rubber. In another embodiment, the elastomer may be a chlorosulfonated polyethylene (CSPE) synthetic rubber Hypalon® (DuPont). In operation, as the gripping fingers close around a specimen container, first the angled alignment nodes 112a, 112b come into contact with the specimen container and operate to push, or otherwise center the specimen container to the centerline 110 of the gripper 34. As the gripping mechanism 34 continues to close, the soft gripping pads 114 or soft surface comes into contact with the specimen container, and compresses and deforms, thereby securely holding the container due to an increase in the friction between the container and gripper 34. When the gripper is fully closed, the container is securely held through contact with both the hard semi-circular surface, or angled nodes 112a, 112b, and the compressed soft gripping pad 114. The container is securely centered and retained by the four parallel hard gripping surfaces created by the first and second nodes 112a, 112b, thereby establishing, or ensuring, proper co-axial alignment of the specimen container with the centerline of the gripping mechanism or gripper. If the container is only in contact with the soft pad 114, the compliance of the soft pad 114 may allow the container to twist or rotate in a an axis normal to the container centerline.

In accordance with another embodiment, the top and bottom gripper fingers 36a, 36b may move independently to accommodate for any vertical misalignment of the specimen container during gripping. If the gripping mechanism is not properly aligned with the centerline of the container, the finger that first comes in contact with the container will help to realign and center the container along the gripper centerline.

Holding Structure Alignment Features

As previously described, the holding structure or racks used in the practice of the present invention can take on a variety of physical configurations. As shown in FIGS., 1-2, 6 and 10-11, the holding structures or racks 22 may comprise a plurality of vertically stacked racks 22 each having one or more individual wells 24 for holding individual specimen containers. As shown best in FIG. 9, as described hereinabove, the holding structure or racks 22 may include one or more fiducials 26 for establishing the initial, or home, position of the robotic transfer mechanism relative to the holding structures or racks 22, or more specifically, to the one or more fiducials in the holding structure or racks 22. Knowing the initial, or home position of the robotic transfer mechanism relative to the one or more fiducials allows for determination, or calculation, of the X and Y positions of each individual well 24, thereby establishing, or ensuring proper alignment of the robotic transfer mechanism with the individual wells (i.e., co-axial alignment) during loading of a specimen container into, or unloading of a specimen container from, the individual wells.

Figure 13:
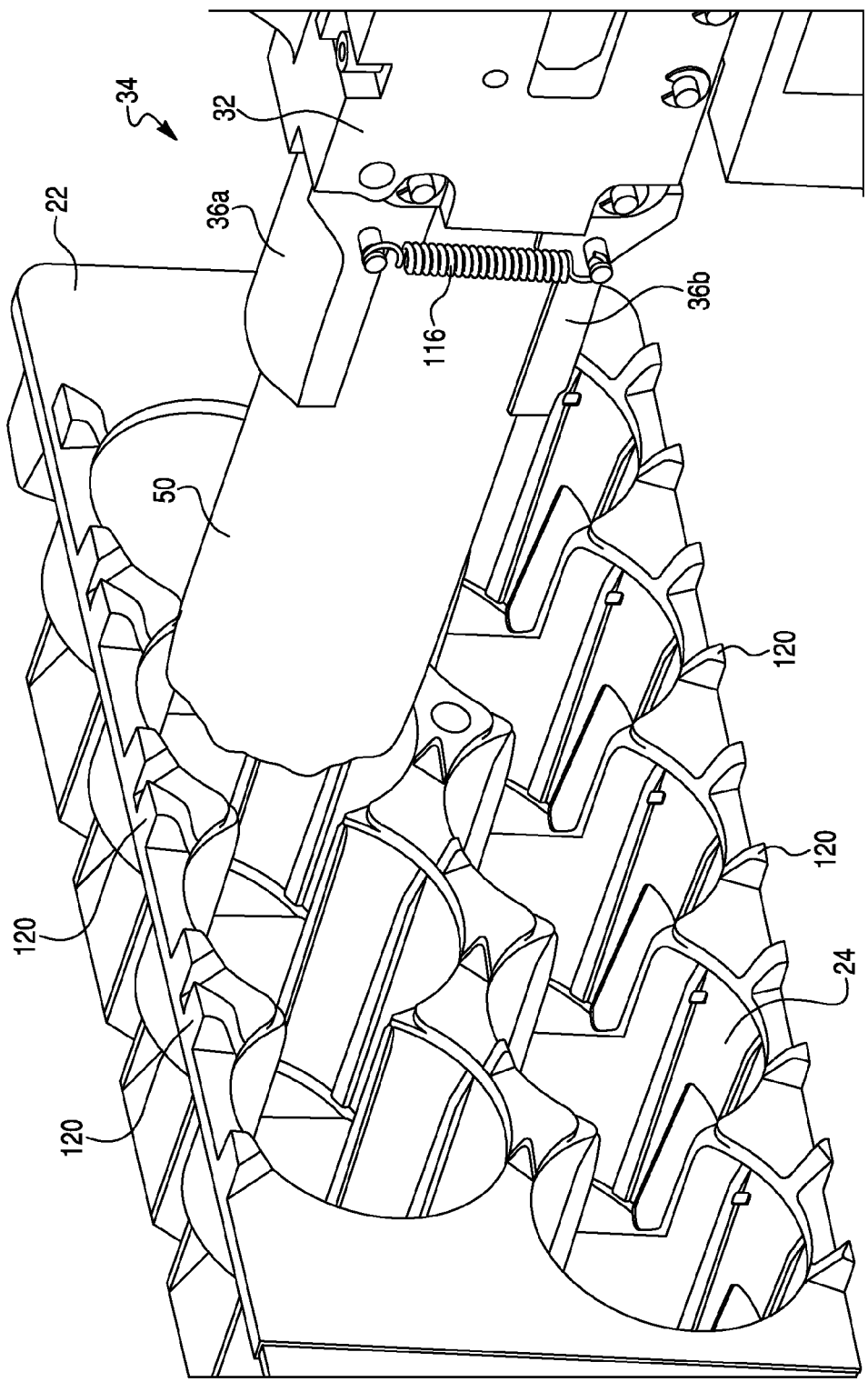
FIG. 13 is a perspective view of a robotic head and gripping mechanism shown loading a specimen container into a well of a holding structure having a lead in ramp in accordance with one embodiment of the invention.

In another aspect, the present invention is also directed to alignment features arranged in conjunction with each individual well to correct for any small misalignment of said specimen container as said container is loaded into an individual holding well. In one embodiment, as shown in FIG. 13, each individual well may include one or more lead-in ramps 120. In accordance with this embodiment, each individual well may include from 2-10 lead-in ramps, from 2-6 lead-in ramps, from 2-4 lead in ramps, 2 lead-in ramps, 3 lead-in ramps, or 4 lead-in ramps. In operation, the one or more lead-in ramps 120 will operate, or help, to guide an individual specimen container 50 into an individual holding well 24, thereby correcting for any misalignment of the specimen container 50 as said container is loaded into said holding well 24.

In another embodiment, as shown in FIG. 14, each individual well may include a continuous lead-in ramp or a continuous lead-in chamfer 124. In operation, the continuous lead-in ramp or a continuous lead-in chamfer 124 will operate, or help, to guide an individual specimen container 50 into an individual holding well 24, thereby correcting for any misalignment of the specimen container 50 as said container is loaded into said holding well 24.

Belt Tensioning Mechanism or Device

In yet another aspect, one or more belt tensioning devices may be used in the practice of this invention to establish and/or maintain proper tension on one or more timing belts or drive belts. As would be readily appreciated by one of skill in the art, timing belts can be used in robotic systems to convert rotary motion of a motor into linear motion. The use of timing belt and pulley system in robotic systems are common because they provide reliability at a low cost. However, to achieve precise positional accuracy, the teeth of the timing belt must properly engage the motor pulley grooves. Proper engagement is dictated by the tension of the belt. Accordingly, timing belts must be properly tensioned to ensure precise location accuracy. An improperly tensioned belt can lead to pre-mature belt, motor, or pulley failures.

As shown in FIGS. 15-18, in one embodiment, a first tensioning device 140 comprises a tensioning device housing 142 coupled to a slidable plate 144 having a pair of slide slots 146 with attachment means or screws 148 for securing the slidable plate 144 to a horizontal or vertical support structures of the transfer mechanism. In operation, the slidable plate 144 is adjustable relative to the horizontal support 40 of the vertical support rail 42 (i.e., the y-axis of the automated transfer mechanism) using the slide slots 146 and associated screws 148. The slide plate 144 is further coupled to an idler pulley 150 which has teeth for engaging and supporting a horizontal timing belt 72.

Figure 17:
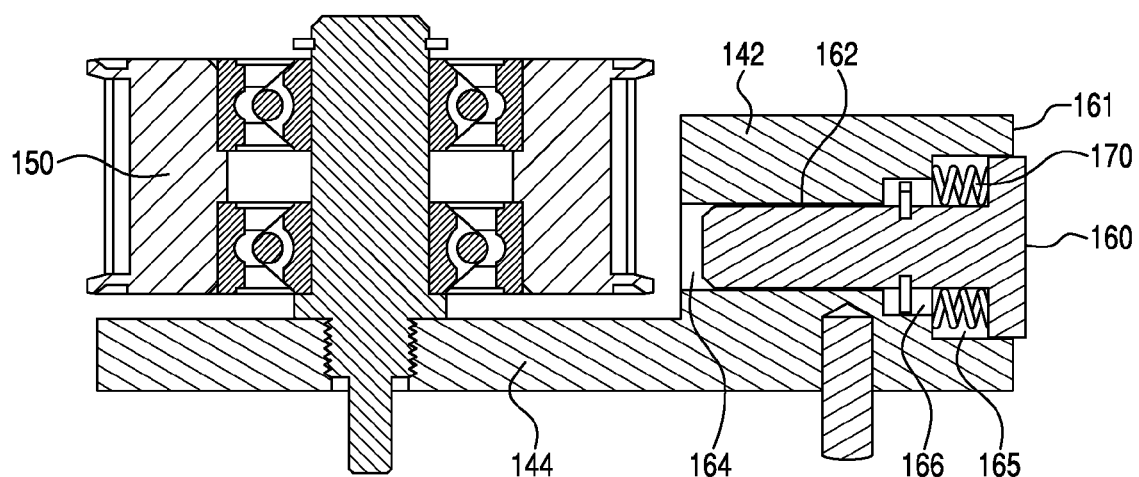
FIG. 17 is a side cross-sectional view of the tensioning device shown in FIGS. and 15A-16.
Figure 18:
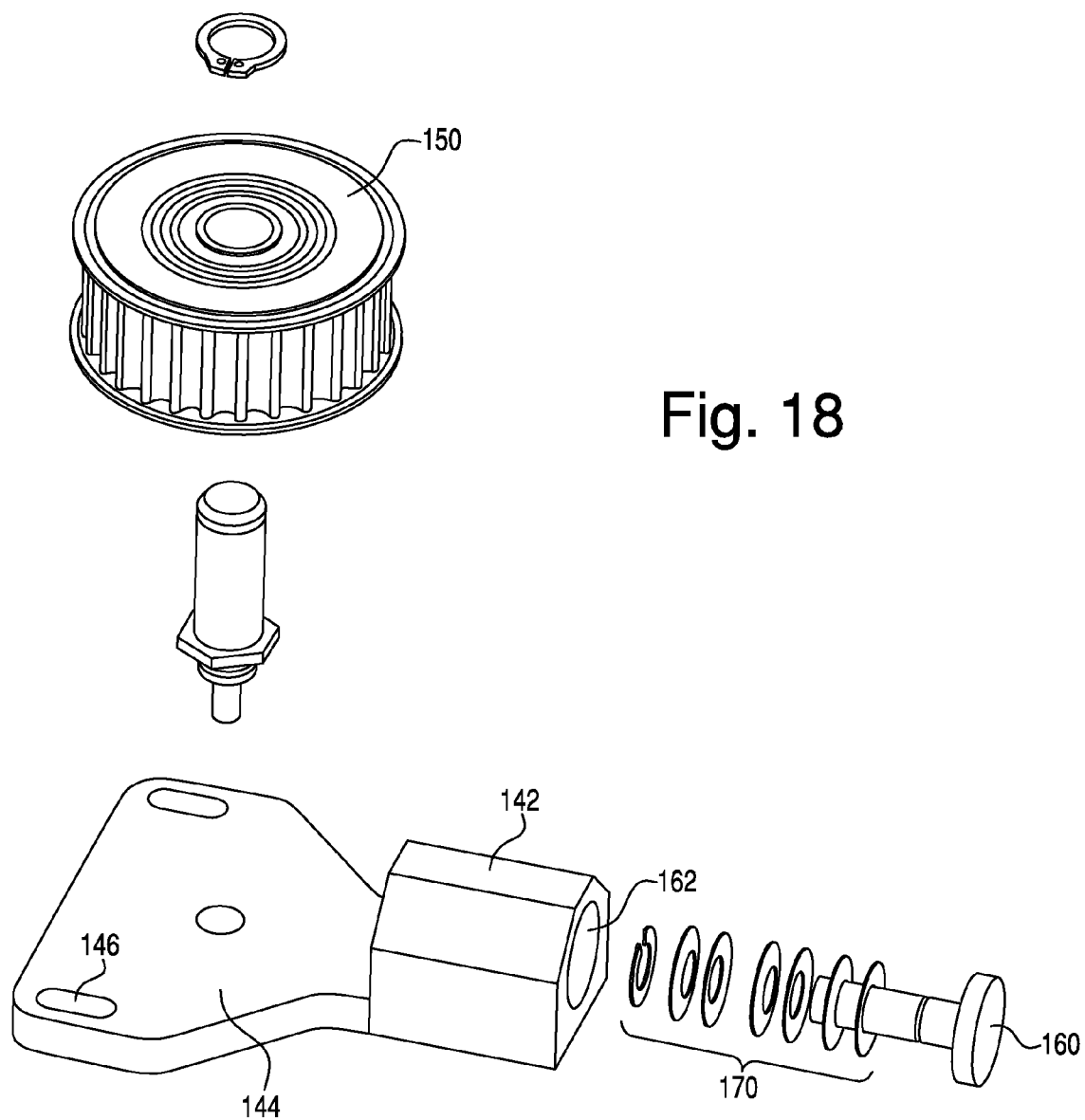
FIG. 18 is an exploded view of the tensioning device shown in FIGS. 15A-17.
Figure 20:
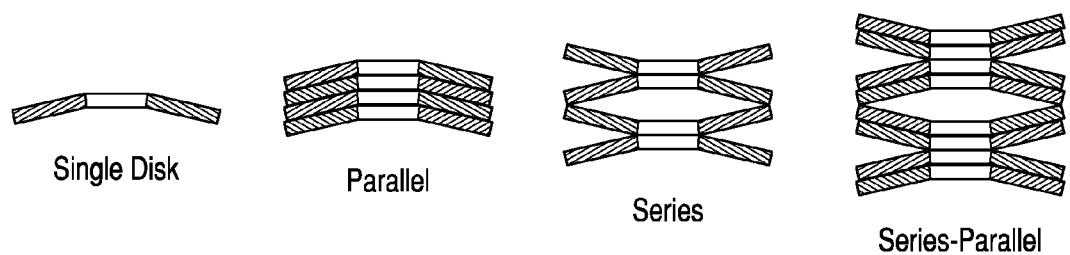
FIG. 20 shows various configurations of Belleville washers, in accordance with certain embodiments of the present invention.

As shown best in FIG. 17, the tensioning device housing 142 further includes a plunger 160 and a counter bore 162. The counter bore 162 comprises an internal bore 164, an intermediate bore 166 and an outer bore 165. The tensioning device housing 142 further comprises a compression mechanism 170 for providing force, and thus, tension to the timing belt 72. In one embodiment, the compression means for providing force may be one or more disk washer, from 2 to 20 disk washers, from 2-10 disk washers, from 4-8 disk washers, or about 6 disk washers. The present applications have realized that disk washers can generate large amounts of force in a compact, or confined area. In general, any known disk washers can be used in the practice of this invention, for example, the disk washers can be Belleville washers. In accordance with this embodiment, the one or more disk washers can be arranged in series, in parallel, or in any combination thereof (see, e.g., FIG. 20). As shown in FIG. 18, the compression mechanism 170 for providing force may comprise a plurality of disk washers (e.g., 6 disk washers) arranged in series. Because the total deflection of a Belleville washer may be extremely small to achieve the desired force, the washers can be stacked to create more deflection while producing the same force. For example, consider a single Belleville washer that generates one unit of force at a deflection of one unit of length. If six of said Belleville washers are stacked in series, they have to be deflected six units of length to achieve one unit of force. The stack of 6 washers has an effective spring rate, k, in units of force/distance, that is $\frac{1}{6}^{th}$ of the single washer. In the application of a tensioner, the tensioning device can be designed such that the proper deflection distance, and thus, the proper force, can be established when a user or technician tightens the threaded screw so that the plunger is flush with the tensioning device housing. The use of a lower spring rate allows for more error in establishing that the plunger is flush, while minimizing the potential error in the applied force. In yet another embodiment, the compression means for providing force may be a compression spring.

Figure 15A:
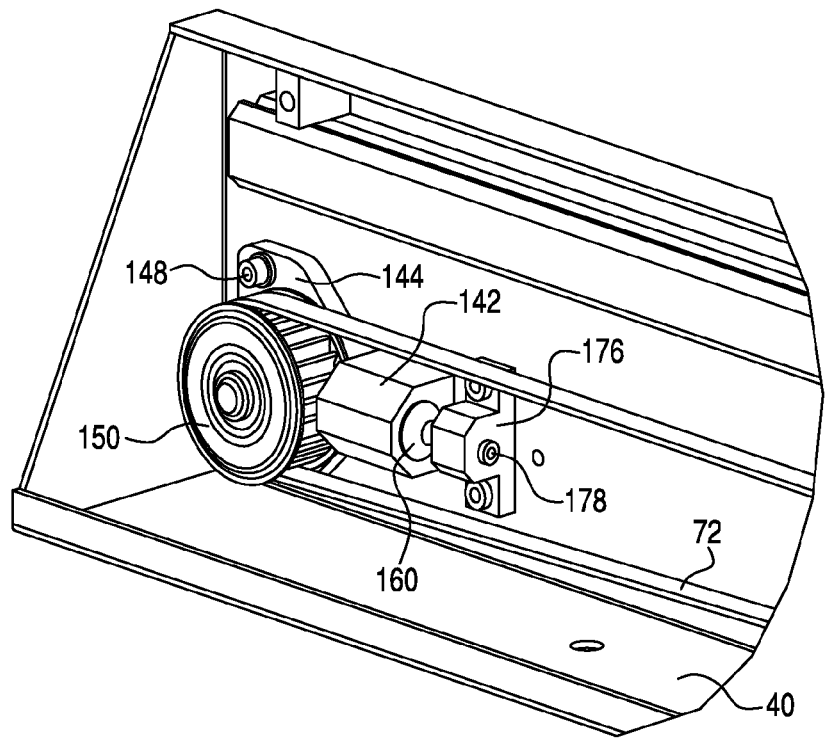
FIG. 15A is a side perspective view of a tensioning device, in accordance with one embodiment of the present invention.
Figure 15B:
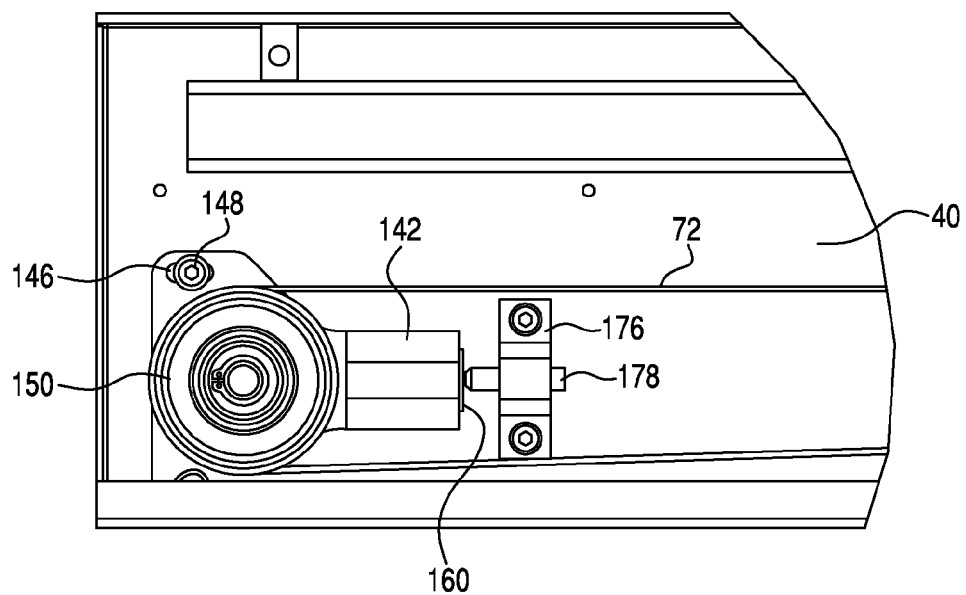
FIG. 15B is a side view of the tensioning device shown in FIG. 15A.
Figure 16:
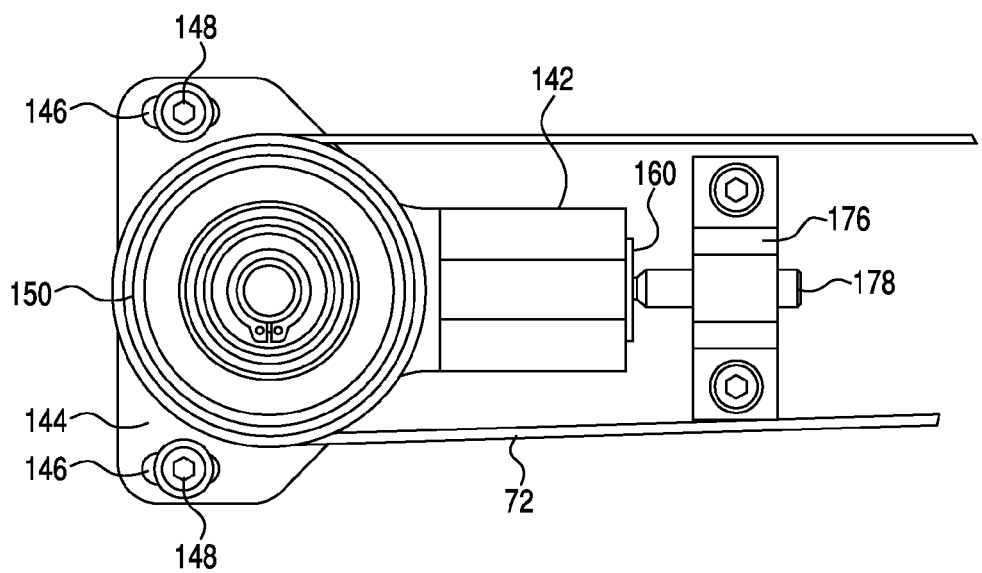
FIG. 16 is a side view of the tensioning device of FIGS. 15A-15B.

As shown best in FIGS. 15 and 16, the tensioning device of this embodiment may further comprise a fixed tension block 176, which is securely attached to the horizontal support 40. As shown, the fixed tension block 176 supports a threaded adjustment screw 178. The threaded adjustment screw 178 can be tightened to compress the compression mechanism 170 for providing force. In yet another embodiment of the present invention, the plunger 160 can be designed such that when the compression mechanism 170 is compressed to the necessary extent for generating the proper belt tension, the face of the plunger will be flush to the leading edge 161 of the tensioning device housing 142 (as best shown in FIG. 17). In this way the tensioning device 140 solves any potential concern about establishing the proper belt tension, as it provides a feature (i.e., the plunger 160 being flush to the leading edge 161 of the fixed tension block housing 142), that instructs the technician when the proper belt tension is achieved.

In operation, a technician can manually turn the threaded adjustment screw 178, or tighten the threaded screw, until the plunger 160 is flush to the leading edge 161 of the fixed tension block housing 142. With the plunger 160 flush against the leading edge 161, the compression means for providing force 170 (i.e., the disk washers arranged in series) are compressed inward at the proper distance to provide the required force or tension to the timing belt 72. Moreover, the generated force slides the slide plate 144, and thus the idler pulley 150, in the opposite direction of the fixed tension block 176 to place the proper amount of tension on the timing belt 72.

In the application of the tensioner, the mounting plate screws 148 are not fully tightened, allowing the plate with the pulley to move along slot 146. As the disk stack compresses, the tension in the belt likewise increases. At the point the plunger is flush, the plate 144 can be secured to the mounting surface by tightening mounting plate screws 148, thereby setting the proper belt tension.

Figure 19:
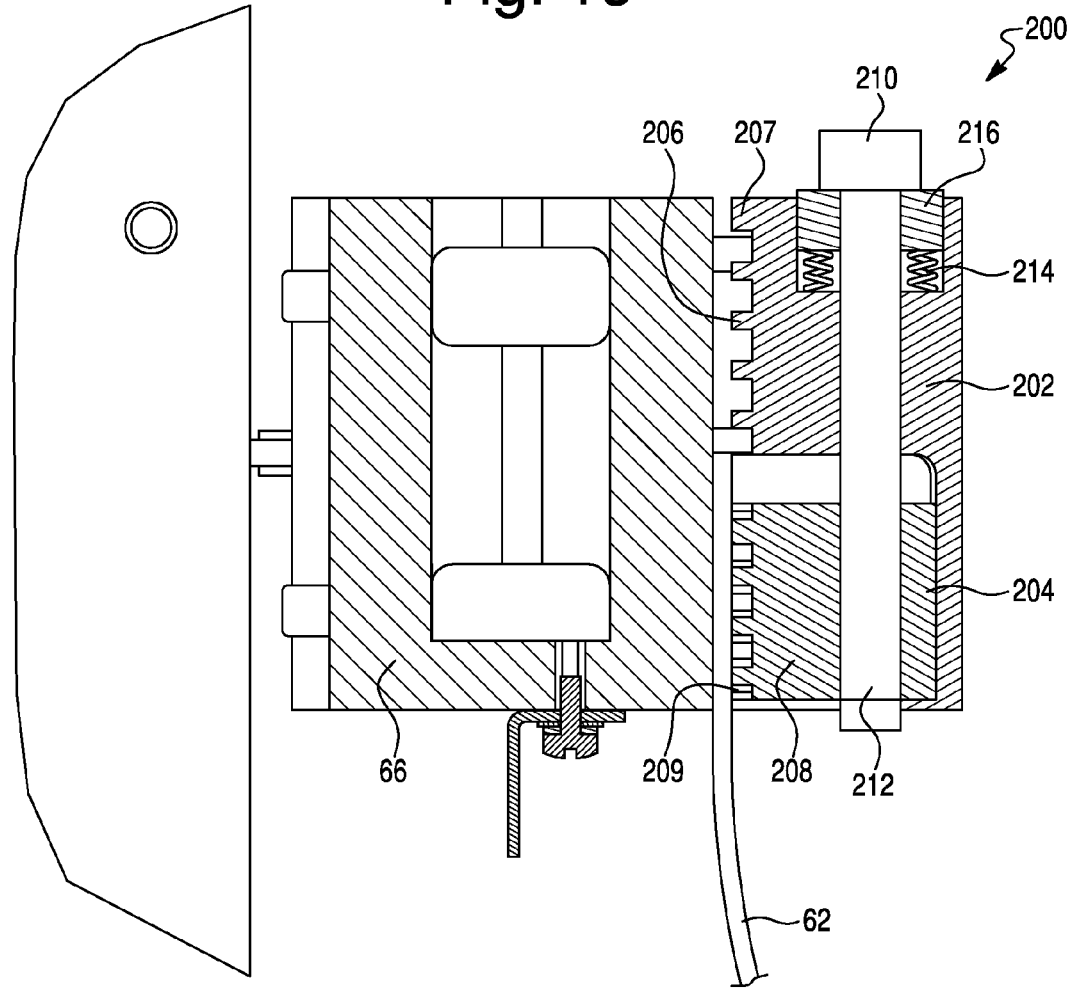
FIG. 19 is a cross-sectional view of a tensioning device, in accordance with another embodiment of the present invention.

FIG. 19 shows a second, or alternative embodiment of a tensioning device 200, in accordance with the present invention. As shown in FIG. 19 the tensioning device 200 of this embodiment includes a stationary block 202 coupled to a carriage 66 for supporting the horizontal slide axis of the robotic transfer mechanism 30, and a slidable block 204, which is adjustable relative to the first stationary block. The first stationary block 202 and the second slidable block 204 further includes teeth 206, 208 on a first edge 207, 209 of the first and second blocks 202, 204, respectively. The teeth 206 of the stationary block 202 engage and securely hold a first end of the timing belt 62 and the teeth 208 of the slidable block 204 engage and securely hold a second or opposite end of the timing belt 62.

The stationary block 202 further includes a threaded plunger 210 aligned with a counter bore 212 in the slidable block 204. When the threaded plunger 210 is tightened, driving the threaded plunger 210 into the counter bore 212 of the slidable block 204, the threaded plunger compresses a compression mechanism 214 for providing force. In accordance with this embodiment, the tensioning device 200 further includes a spacer 216. The tensioner 200 can be designed such that the proper deflection distance, and thus, the proper force, can be established when a user or technician tightens the threaded plunger 210 so that the spacer 216 is flush with the top surface of the stationary block 202. The force generated provides the proper tension to the timing belt 62 by adjusting the distance between the stationary block 202 and the slidable block 204. In one embodiment, the compression mechanism 214 for providing force may be one or more disk washer, from 2 to 20 disk washers, from 2-10 disk washers, from 4-8 disk washers, or about 6 disk washers. The present applications have realized that disk washers can generate large amounts of force in a compact, or compressed area. In general, any known disk washers can be used in the practice of this invention, for example, the disk washers can be Belleville washers. In accordance with this embodiment, the one or more disk washers can be arranged in series, in parallel, or in any combination thereof (see, e.g., FIG. 20). In another embodiment, the compression mechanism for providing force may comprise 6 disk washers arranged in series. In yet another embodiment, the compression mechanism for providing force may be a compression spring.

In operation, the threaded plunger 210 can be tightened, or screwed into the counter bore 212 thereby moving the slidable block 204 in a first direction towards the stationary block 202, thereby bringing the slidable block 204 closer to the stationary block 202. Tightening the threaded plunger 210 compress the compression mechanism 214 providing force that results in tension on the timing belt 62. In one embodiment, after proper adjustment, the slidable block 204 can be fixed, or locked, relative to the stationary block 202 using a screw.

Controller and User Interface

The detection system 2 will include a system controller (e.g., a computer control system) (not shown) and firmware for controlling the various operations and mechanisms of the system. Typically, the system controller and firmware for controlling the operation of the various mechanisms of the system can be any known conventional controller and firmware known to those of skill in the art. In one embodiment, the controller and firmware will performs all operations necessary for controlling the various mechanisms of the system, including: automated loading, automated transfer, automated detection and/or automated unloading of specimen containers within the system. The controller and firmware will also provide for identification and tracking of specimen containers within the system. In another embodiment, the controller and firmware will control the alignment of the transfer mechanism. For example, the controller can provide precise locational control of the robotic transfer mechanism to locate and align the robotic transfer mechanism with other mechanisms or devices that interface with the robotic transfer mechanism, such as, the individual wells of the holding structure or racks, the indexer, the container return port and/or the waste chute.

In another embodiment, as previously disclosed hereinabove, the controller and firmware can use to calculate the precise X and Y positions, or coordinates, of each individual well in the holding structure relative to the gripping mechanism of the robotic transfer mechanism. In accordance with this embodiment, once the laser alignment device and holding structure or racks are properly aligned, relative to one another, as described elsewhere herein, the controller can then precisely calculate the exact X and Y position of each individual well in the holding structure or racks. Knowing the precise location of each well allows the controller to precisely control the movement of the robotic head for proper loading and unloading of a specimen container, into or from, a specific well in the holding structure or rack.

The detection system 2 may also include a user interface 14 and associated computer control system for operating the system, including, the loading mechanism, transfer mechanism, racks, agitation equipment, incubation apparatus, and receiving measurements from the detection units. The user interface 14 may also provide an operator or laboratory technician with status information regarding containers loaded into the detection system. The user interface may include one or more of the following features: (1) Touch screen display; (2) Keyboard on touch screen; (3) System status; (4) Positives alert; (5) Communications to other systems (DMS, LIS, BCES & other detection or identification Instruments); (6) Container or bottle status; (7) Retrieve containers or bottles; (8) Visual and audible Positive Indicator; (9) USB access (back ups and external system access); and (10) Remote Notification of Positives, System Status and Error Messages.

That which is claimed is:

1. An alignment system for establishing and/or maintaining alignment of an automated robotic transfer mechanism in an automated detection system relative to a holding structure for holding one or more specimen containers, comprising:
    (a) an automated detection system for processing specimen containers, said detection system having a housing enclosing an interior chamber;
    (b) a holding structure within said interior chamber said holding structure having one or more holding wells for holding individual specimen containers, wherein said holding structure further comprises one or more fiducials;
    (c) an automated robotic transfer mechanism for the automated transfer of said specimen container within said interior chamber, said automated robotic transfer mechanism further comprising a gripping mechanism and a laser alignment device, said laser alignment device operable to detect said one or more fiducials and thereby determine the home position of said automated transfer mechanism relative to said holding structure, and wherein said laser alignment device is attached to an adjustable block, said adjustable block having a pair of slots and a pair of screws operable for adjusting said laser alignment device relative to said robotic transfer mechanism; and
    (d) a controller for determining the x and y positions of said one or more holding wells relative to the home position of said automated transfer mechanism relative to said holding structure.

2. The alignment system of claim 1, wherein said laser alignment device further comprises an alignment tool, said alignment tool comprising a fiducial operable to establish alignment of said laser alignment device relative to said robotic transfer mechanism.

3. The alignment system of claim 2, wherein said laser alignment device further comprises a first adjustment mechanism for adjustment of said laser alignment device relative to said fiducial of said alignment tool.

4. The alignment system of claim 2, wherein said adjustable laser further comprises a second adjustment mechanism for adjustment of said laser alignment device relative to said fiducial of said alignment tool.

5. The alignment system of claim 2, wherein said alignment tool further comprises a removable positioning piece, said removable positioning piece comprising a horizontal indicator line and a vertical indicator line operable to establishing alignment of said gripping mechanism, in the x-axis and y-axis, relative to a container pick-up station.

6. The alignment system of claim 1, wherein said individual holding wells further comprises a lead in ramp to guide an individual specimen container into said holding well, and thereby correcting for any misalignment of said specimen container as said container is loaded into said holding well.

7. The alignment system of claim 6, wherein said lead in ramp comprise a plurality of angled lead in nodes.

8. The alignment system of claim 6, wherein said lead in ramp comprise a continuous tapered lead in ramp.

9. The alignment system of claim 1, further comprising a belt tensioning device operable to provide tension to one or more timing belts.

10. The belt tensioning device of claim 9, wherein said belt tensioning device further comprises a compression mechanism, wherein said compression mechanism is a compression spring.

11. The belt tensioning device of claim 9, wherein said belt tensioning device further comprises a compression mechanism, said compression mechanism comprising one or more disk washers, wherein said disk washers are arranged in series, in parallel, or a combination thereof.

12. The alignment system of claim 1, wherein said gripping mechanism comprising from 2 to 6 gripping fingers operable to securely grip and/or hold said specimen container.

13. The alignment system of claim 12, wherein said gripping fingers comprise 2 opposable semi-circular shaped gripping fingers, wherein said semi-circular shaped gripping fingers define a gripping cavity operable to securely grip and/or hold said specimen container.

14. The alignment system of claim 13, wherein said semi-circular shaped gripping fingers further comprise an opposable pair of angled alignment nodes operable to center said specimen container within said gripping cavity.

15. The alignment system of claim 14, wherein said gripping fingers further comprises an elastomeric gripping pad operable to securely hold said container.

16. A method for establishing and/or maintaining alignment of an automated transfer mechanism relative to a holding structure, the method comprising:
    (a) providing an automated robotic transfer mechanism having a robotic head, a gripping mechanism for gripping a specimen container around a centerline of said gripping mechanism, and a laser alignment device attached to the robotic head;
    (b) providing a holding structure comprising a plurality of holding wells and one or more fiducials;
    (c) detecting said one or more fiducials with said laser alignment device, thereby setting a home position for said automated robotic transfer mechanism relative to said holding structure; and (d) determining the x- and y-positions of said one or more holding wells using a controller.

17. The method of claim 16, wherein said adjustable laser alignment device is aligned with respect to said robotic transfer mechanism using an alignment tool.

18. The method of claim 17, wherein said alignment tool further comprises a fiducial, and wherein said adjustable laser alignment device is adjusted to detect said fiducial to establish alignment of said laser alignment device with respect to said robotic transfer mechanism, and thereby with said gripping mechanism.

19. The method of claim 17, wherein said alignment tool further comprises a removable positioning piece, said removable positioning piece comprising a horizontal indicator line and a vertical indicator line, wherein said method further comprises using said horizontal indicator line and a vertical indicator line to align of said gripping mechanism, in the x-axis and y-axis, relative to a container pick-up station.

20. A belt tensioning device for maintaining proper tension on a transfer mechanism timing belt, comprising:
   (a) a robotic transfer mechanism having at least one axis, a robotic head movable along said at least one axis, and a timing belt; and
   (b) a tensioning device operable to provide tension to said timing belt, said tensioning device comprising:
      i. a slide plate coupled to a tensioner housing and to an idler pulley;
      ii. a fixed block and threaded shaft, wherein said threaded shaft is movable relative to said fixed block;
      iii. a tensioner housing having a counter bore, a plunger and a compression mechanism operable to provide a force, wherein said plunger is movable relative to said counter bore and said compression mechanism; and
   wherein said threaded shaft is operable to drive said plunger into said counter bore, thereby compressing said compression mechanism and provide tension to said timing belt.

21. The belt tensioning device of claim 20, wherein said compression mechanism is a spring.

22. The belt tensioning device of claim 20, wherein said compression mechanism comprises one or more disk washers, wherein said disk washers are arranged in series, in parallel, or a combination thereof.

23. A belt tensioning device for maintaining proper tension on a transfer mechanism timing belt, comprising:
   (a) a robotic transfer mechanism having at least one axis, a robotic head movable along said at least one axis, and a timing belt; and
   (b) a tensioning device operable to provide tension to said timing belt, said tensioning device comprising:
      i. a stationary block having a threaded plunger, a compression mechanism and a plurality of teeth operable to engage a first end of said timing belt, wherein said stationary block is coupled to a carriage supporting the robotic transfer mechanism; and
      iv. a slidable block having a counter bore, a threaded plunger and a plurality of teeth for engaging a second end of said timing belt, wherein said plunger is movable relative to said counter bore and said compression mechanism; and
   wherein said threaded plunger is operable to drive said plunger into said counter bore, thereby compressing said compression mechanism and provide tension to said timing belt.

24. The belt tensioning device of claim 23, wherein said compression mechanism is a spring.

25. The belt tensioning device of claim 23, wherein said compression mechanism comprises one or more disk washers, wherein said disk washers are arranged in series, in parallel, or a combination thereof.

\* \* \* \* \*